(12) United States Patent
Kadowaki et al.

(10) Patent No.: US 7,741,080 B2
(45) Date of Patent: Jun. 22, 2010

(54) ADIPONECTIN EXPRESSION-INDUCING AGENTS AND USES THEREOF

(75) Inventors: Takashi Kadowaki, Tokyo (JP); Toshimasa Yamauchi, Tokyo (JP); Shoko Kitajima, Tokyo (JP); Yusuke Ito, Saitama (JP)

(73) Assignees: Nissan Chemical Industries, Ltd., Tokyo (JP); Toudai TLO, Ltd, Tokyo (JP)

( * ) Notice: Subject to any disclaimer, the term of this patent is extended or adjusted under 35 U.S.C. 154(b) by 285 days.

(21) Appl. No.: 10/594,969

(22) PCT Filed: Mar. 31, 2005

(86) PCT No.: PCT/JP2005/006357

§ 371 (c)(1),
(2), (4) Date: Mar. 14, 2007

(87) PCT Pub. No.: WO2005/094866

PCT Pub. Date: Oct. 13, 2005

(65) Prior Publication Data

US 2007/0203061 A1 Aug. 30, 2007

Related U.S. Application Data

(60) Provisional application No. 60/557,708, filed on Mar. 31, 2004.

(51) Int. Cl.
C12P 19/34 (2006.01)
C12N 15/00 (2006.01)
C07H 21/04 (2006.01)

(52) U.S. Cl. .................. 435/91.1; 536/23.1; 435/320.1; 435/455; 435/325

(58) Field of Classification Search ........................ None
See application file for complete search history.

(56) References Cited

U.S. PATENT DOCUMENTS 6,582,909 B1 * 6/2003 Bougueleret et al. ........... 435/6
7,365,170 B2 * 4/2008 Cooper et al. ................ 530/399
2004/0241802 A1 12/2004 Kadowaki et al.

FOREIGN PATENT DOCUMENTS

| EP | 1 577 388 | 9/2005 |
|---|---|---|
| WO | WO 00/26363 | 5/2000 |
| WO | WO 01/32868 | 5/2001 |
| WO | WO /02/101075 A2 * | 12/2002 |
| WO | WO 2004/058970 | 7/2004 |
| WO | WO 2004/061108 | 7/2004 |
| WO | WO 2004/078741 | 9/2004 |
| WO | WO 2005/094866 | 10/2005 |

OTHER PUBLICATIONS

Post et al., Gene therapy versusprotein-based therapy: a matter of pharmacokinetics. Drug Discovery Today, 6, 769-770, 2001.*
Berg et al. Nat Med. (Aug. 2001) 7(8): 947-53.
Friedman Nature (Apr. 6, 2000) 404(6778): 632-4.
Hotamisligil et al. Science (Jan. 1, 1993) 259(5091): 87-91.
Hotta et al. Arterioscler Thromb Vasc Biol. (Jun. 2000) 20(6): 1595-9.
Hu et al. J Biol Chem. (May 3, 1996) 271(18): 10697-703.
Kersten et al. Nature. (May 25, 2000) 405(6785): 421-4.
Kubota et al. J Biol Chem. (Jul. 19, 2002) 277(29): 25863-6.
Maeda et al. Biochem Biophys Res Commun. (Apr. 16, 1996) 221(2): 286-9.
Maeda et al. Nat Med. (Jul. 2002) 8(7): 731-7.
Matsuda et al. J Biol Chem. (Oct. 4, 2002) 277(40): 37487-91.
Nakano et al. J Biochem (Tokyo) (Oct. 1996) 120(4): 803-12.
Okamoto et al. Circulation. (Nov. 26, 2002) 106(22): 2767-70.
Ouchi et al. Circulation. (Feb. 27, 2001) 103(8): 1057-63.
Scheer et al. Embo J. (Jul. 15, 1996) 15(14): 3566-78.
Scherer et al. J Biol Chem. (Nov. 10, 1995) 270(45): 26746-9.
Shimoura et al. Nat Med. (Jul. 1996) 2(7): 800-3.
Shulman J Clin Invest. (Jul. 2000) 106(2): 171-6.
Spiegelman et al. Cell (Nov. 1, 1996) 87(3): 377-89.
Steppan et al. Nature (Jan. 18, 2001) 409(6818): 307-12.
Tomas et al. Proc Natl Acad Sci USA. (Dec. 10, 2002) 99(25): 16309-13.

(Continued)

*Primary Examiner*—Christine J Saoud
*Assistant Examiner*—Elly-Gerald Stoica
(74) *Attorney, Agent, or Firm*—Hunton & Williams LLP

(57) ABSTRACT

The present invention provides adiponectin expression-inducing agents, and therapeutic agents using the same for obesity and obesity-related diseases such as cardiovascular diseases or metabolic diseases, as well as methods of searching for adiponectin expression-inducing agents.

KLF9, which can bind to the 32-bp fragment of position −188 to position −157 from the adiponectin expression start site, was demonstrated to enhance adiponectin promoter activity. Therefore, the present invention uses KLF9 as an adiponectin expression-inducing agent, and suggests that KLF9 replenishment therapy is useful for preventing and/or treating obesity or obesity-related diseases including metabolic diseases such as insulin resistance and type II diabetes, and cardiovascular diseases.

9 Claims, 11 Drawing Sheets

OTHER PUBLICATIONS

Wess FASEB J. (Apr. 1997) 11(5): 346-54.
White et al. J Biol Chem. (May 5, 1992) 267(13): 9210-13.
Yamauchi et al. Nat Med. (Aug. 2001) 7(8): 941-6.
Yamauchi et al. Nat Med. (Nov. 2002) 8(11): 1288-95.
Yamauchi et al. J Biol Chem. (Jan. 24, 2003) 278(4): 2461-8.
Yamauchi et al. Nature. (Jun. 12, 2003) 443(6941): 762-9.
Yokomizo et al. Nature (Jun. 5, 1997) 387(6633): 620-4.
Yokota et al. Blood (Sep. 1, 2000) 96(5): 1723-32.
Zhang et al. Nature (Dec. 1, 1994) 372(6505): 425-35.
Das et al. (2001) "Chromosomal Localization, Expression Patter, and Promoter Analysis of the Mouse Gene Encoding Adipocyte-Specific Secretory Protein Acrp30." Biochem. Biophys. Res. Commun. 280: 1120-1129.
Freubis et al. (2001) Proteolytic Cleavage product of 30-kDa adipocyte complement-related protein increases fatty acid oxidation in muscle and causes weight loss in mice. Proc. Natl. Acad. Sci. USA 98(4): 2005-2010.
Imhof et al. (1999) "Transcriptional Regulation of the AP-2a Promoter by BTEB-1 and AP-2rep, a Novel wt-l/egr-Related Zinc Finger Repressor." Mol. Cell. Biol. 19(1): 194-204.
International Searching Authority Report (PCT/ISA/210) mailed May 10, 2005.
Database Unit Pro Online Accession No. Q8CEC4, EBI, Mar. 1, 2003.
Supplementary European Search Report issued in European Application No. EP 05 72 7594, dated Jun. 30, 2009.

* cited by examiner

FIG. 7
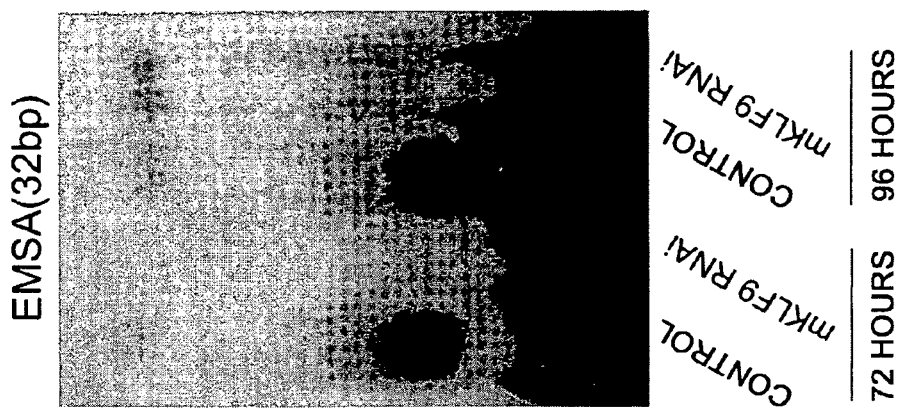
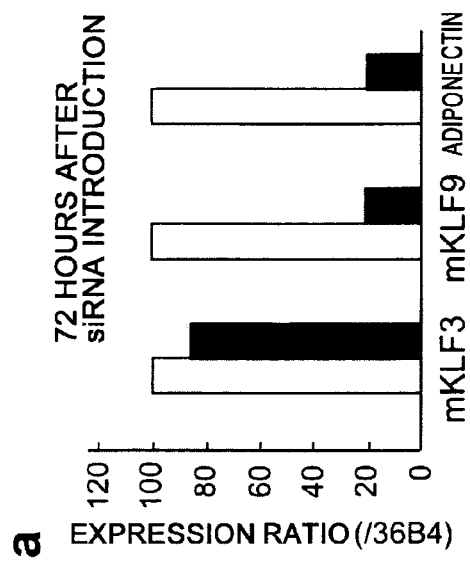

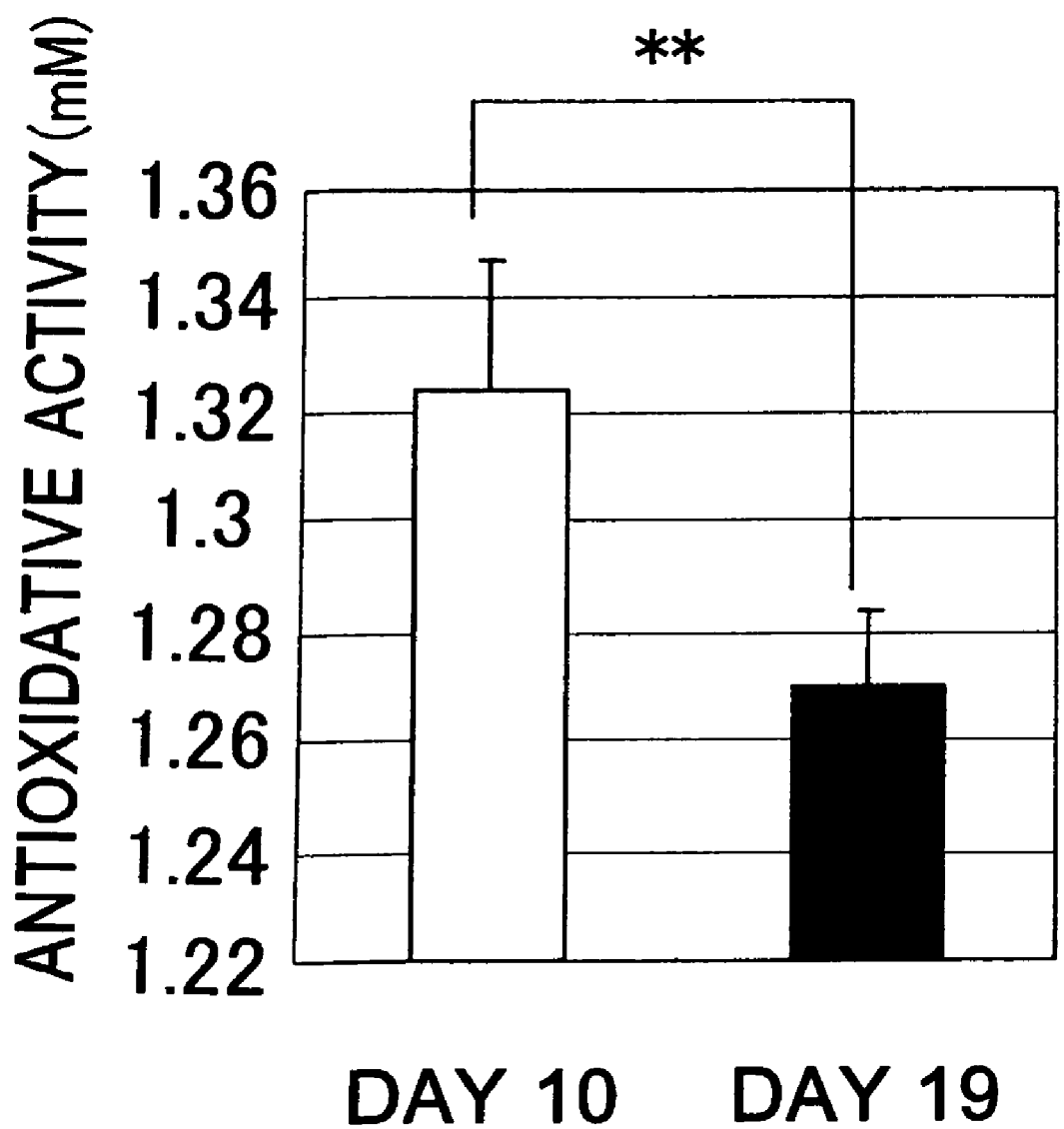

SEQUENCE LISTING

<160> NUMBER OF SEQ ID NOS: 7

<210> SEQ ID NO 1
<211> LENGTH: 735
<212> TYPE: DNA
<213> ORGANISM: Mus musculus

<400> SEQUENCE: 1

```
atgtccgcgg ccgcctacat ggacttcgtg gctgcccagt gtctggtttc catctccaac      60
cgcgccgccg tgccggagca cggggggcgct ccggaagccg agcggctgcg actacctgag     120
cgcgaggtga ccaaggaaca cggtgacccg ggggacacct ggaaggatta ttgcacgctg     180
gtcactatcg ccaagagctt gttggacctc aacaaatacc gacccatcca gaccccctcg     240
gtgtgcagcg acagtctgga gagtcccgat gaggatatag gatccgacag cgacgtgacc     300
```

```
accgaatctg ggtcgagtcc ttcccacagc ccggaggaga gacaggattc tggcagcgcg      360
cccagcccac tctccctcct ccactctgga gtggcttcga aggggaaaca cgcctccgaa      420
aagaggcaca agtgccccta cagtggctgt gggaaagtct atggaaaatc ctcccatctt      480
aaagcccatt acagagtgca tacaggtgaa cggcccttc cctgcacgtg ccagactgc       540 cttaaaaagt tctcgcgctc ggatgagctg accgccact accggaccca cactggggaa      600
aagcagttcc gttgcccact gtgtgagaag agattcatga ggagtgacca tctcaccaag      660
catgcccggc gtcacaccga gttccatccc agcatgatca agagatcaaa aaaggctctt      720
gccagcccct tgtga                                                      735
```

<210> SEQ ID NO 2
<211> LENGTH: 244
<212> TYPE: PRT
<213> ORGANISM: Mus musculus

<400> SEQUENCE: 2

```
Met Ser Ala Ala Ala Tyr Met Asp Phe Val Ala Ala Gln Cys Leu Val
1               5                   10                  15

Ser Ile Ser Asn Arg Ala Ala Val Pro Glu His Gly Gly Ala Pro Glu
                20                  25                  30

Ala Glu Arg Leu Arg Leu Pro Glu Arg Glu Val Thr Lys Glu His Gly
            35                  40                  45

Asp Pro Gly Asp Thr Trp Lys Asp Tyr Cys Thr Leu Val Thr Ile Ala
        50                  55                  60

Lys Ser Leu Leu Asp Leu Asn Lys Tyr Arg Pro Ile Gln Thr Pro Ser
65                  70                  75                  80

Val Cys Ser Asp Ser Leu Glu Ser Pro Asp Glu Asp Ile Gly Ser Asp
                85                  90                  95

Ser Asp Val Thr Thr Glu Ser Gly Ser Ser Pro Ser His Ser Pro Glu
            100                 105                 110

Glu Arg Gln Asp Ser Gly Ser Ala Pro Ser Pro Leu Ser Leu Leu His
        115                 120                 125

Ser Gly Val Ala Ser Lys Gly Lys His Ala Ser Glu Lys Arg His Lys
130                 135                 140

Cys Pro Tyr Ser Gly Cys Gly Lys Val Tyr Gly Lys Ser Ser His Leu
145                 150                 155                 160

Lys Ala His Tyr Arg Val His Thr Gly Glu Arg Pro Phe Pro Cys Thr
                165                 170                 175

Trp Pro Asp Cys Leu Lys Lys Phe Ser Arg Ser Asp Glu Leu Thr Arg
            180                 185                 190

His Tyr Arg Thr His Thr Gly Glu Lys Gln Phe Arg Cys Pro Leu Cys
        195                 200                 205

Glu Lys Arg Phe Met Arg Ser Asp His Leu Thr Lys His Ala Arg Arg
    210                 215                 220

His Thr Glu Phe His Pro Ser Met Ile Lys Arg Ser Lys Lys Ala Leu
225                 230                 235                 240

Ala Ser Pro Leu
```

<210> SEQ ID NO 3
<211> LENGTH: 9229
<212> TYPE: DNA
<213> ORGANISM: Homo sapiens
<220> FEATURE:
<221> NAME/KEY: misc_feature

```
<222> LOCATION: (27)..(27)
<223> OTHER INFORMATION: n is a, c, g, or t
<220> FEATURE:
<221> NAME/KEY: misc_feature
<222> LOCATION: (97)..(97)
<223> OTHER INFORMATION: n is a, c, g, or t
<220> FEATURE:
<221> NAME/KEY: misc_feature
<222> LOCATION: (204)..(204)
<223> OTHER INFORMATION: n is a, c, g, or t
<220> FEATURE:
<221> NAME/KEY: misc_feature
<222> LOCATION: (207)..(207)
<223> OTHER INFORMATION: n is a, c, g, or t
<220> FEATURE:
<221> NAME/KEY: misc_feature
<222> LOCATION: (281)..(281)
<223> OTHER INFORMATION: n is a, c, g, or t
<220> FEATURE:
<221> NAME/KEY: misc_feature
<222> LOCATION: (677)..(677)
<223> OTHER INFORMATION: n is a, c, g, or t
<220> FEATURE:
<221> NAME/KEY: misc_feature
<222> LOCATION: (681)..(681)
<223> OTHER INFORMATION: n is a, c, g, or t
<220> FEATURE:
<221> NAME/KEY: misc_feature
<222> LOCATION: (3260)..(3260)
<223> OTHER INFORMATION: n is a, c, g, or t
<220> FEATURE:
<221> NAME/KEY: misc_feature
<222> LOCATION: (3262)..(3262)
<223> OTHER INFORMATION: n is a, c, g, or t
<220> FEATURE:
<221> NAME/KEY: misc_feature
<222> LOCATION: (3274)..(3274)
<223> OTHER INFORMATION: n is a, c, g, or t
<220> FEATURE:
<221> NAME/KEY: misc_feature
<222> LOCATION: (3297)..(3297)
<223> OTHER INFORMATION: n is a, c, g, or t
<220> FEATURE:
<221> NAME/KEY: misc_feature
<222> LOCATION: (3311)..(3311)
<223> OTHER INFORMATION: n is a, c, g, or t
<220> FEATURE:
<221> NAME/KEY: misc_feature
<222> LOCATION: (3313)..(3313)
<223> OTHER INFORMATION: n is a, c, g, or t
<220> FEATURE:
<221> NAME/KEY: misc_feature
<222> LOCATION: (3318)..(3318)
<223> OTHER INFORMATION: n is a, c, g, or t
<220> FEATURE:
<221> NAME/KEY: misc_feature
<222> LOCATION: (3338)..(3338)
<223> OTHER INFORMATION: n is a, c, g, or t
<220> FEATURE:
<221> NAME/KEY: misc_feature
<222> LOCATION: (3347)..(3347)
<223> OTHER INFORMATION: n is a, c, g, or t
<220> FEATURE:
<221> NAME/KEY: misc_feature
<222> LOCATION: (3356)..(3356)
<223> OTHER INFORMATION: n is a, c, g, or t
<220> FEATURE:
<221> NAME/KEY: misc_feature
<222> LOCATION: (3389)..(3389)
<223> OTHER INFORMATION: n is a, c, g, or t
<220> FEATURE:
<221> NAME/KEY: misc_feature
<222> LOCATION: (3412)..(3412)
<223> OTHER INFORMATION: n is a, c, g, or t
<220> FEATURE:
<221> NAME/KEY: misc_feature
<222> LOCATION: (3422)..(3422)
<223> OTHER INFORMATION: n is a, c, g, or t
<220> FEATURE:
```

```
<221> NAME/KEY: misc_feature
<222> LOCATION: (3424)..(3424)
<223> OTHER INFORMATION: n is a, c, g, or t
<220> FEATURE:
<221> NAME/KEY: misc_feature
<222> LOCATION: (3426)..(3426)
<223> OTHER INFORMATION: n is a, c, g, or t
<220> FEATURE:
<221> NAME/KEY: misc_feature
<222> LOCATION: (3430)..(3430)
<223> OTHER INFORMATION: n is a, c, g, or t
<220> FEATURE:
<221> NAME/KEY: misc_feature
<222> LOCATION: (3459)..(3459)
<223> OTHER INFORMATION: n is a, c, g, or t
<220> FEATURE:
<221> NAME/KEY: misc_feature
<222> LOCATION: (3477)..(3477)
<223> OTHER INFORMATION: n is a, c, g, or t
<220> FEATURE:
<221> NAME/KEY: misc_feature
<222> LOCATION: (3507)..(3507)
<223> OTHER INFORMATION: n is a, c, g, or t
<220> FEATURE:
<221> NAME/KEY: misc_feature
<222> LOCATION: (3542)..(3542)
<223> OTHER INFORMATION: n is a, c, g, or t
<220> FEATURE:
<221> NAME/KEY: misc_feature
<222> LOCATION: (3892)..(3892)
<223> OTHER INFORMATION: n is a, c, g, or t
<220> FEATURE:
<221> NAME/KEY: misc_feature
<222> LOCATION: (4344)..(4344)
<223> OTHER INFORMATION: n is a, c, g, or t
<220> FEATURE:
<221> NAME/KEY: misc_feature
<222> LOCATION: (4551)..(4551)
<223> OTHER INFORMATION: n is a, c, g, or t
<220> FEATURE:
<221> NAME/KEY: misc_feature
<222> LOCATION: (5699)..(5699)
<223> OTHER INFORMATION: n is a, c, g, or t

<400> SEQUENCE: 3
```

| | | | | | |
|---|---|---|---|---|---|
| aacatacata | tcttggtgag | ggattanccc | atataatgaa | cagagtagag | aatcctgaaa | 60
| gagatcccaa | tgcatttgaa | aaatgggtat | atgaaanagt | catttaaaaa | atagaaccaa | 120
| aaagataaat | atccattaaa | aaggagggtg | ttgagtcccc | taactaagaa | tatatatata | 180
| tatatatata | tatatatagc | tagnttnccc | tttaattccc | tctgaagaag | gaattgctta | 240
| tgcaagactc | caaagctgag | aaccagattg | tctttcagtg | ntcatgcagc | ctggaaagcc | 300
| cccaccttat | gtaccaatag | attgtgaagc | aatcaaagac | tactacatac | actttaaagc | 360
| caaccagaaa | gactccttcc | cttccaagta | tcttctaccc | gattggaact | agaatatgtc | 420
| accctgaaag | aacactcacc | aaagattggc | ttaagtcttc | ctcctttttag | tctgtaaaac | 480
| ttactcttct | aggctggcgc | agtggctcac | gcctataatc | ccagcacttt | gggaagctaa | 540
| ggcgggtgga | tcacctgagg | tcaggagttc | gagaccagcc | tggcaaacat | ggtaaaaccc | 600
| cgtctttact | aaaaatacaa | aaattagctg | ggaatagtgg | caggtgcctg | tagtcccagc | 660
| tgctcaggag | gctgagncag | nagaatcgct | tcaacctggg | aagcggagct | tgcagtgagc | 720
| tgagatcgtg | ctactgcact | ccagcctggg | caagagtgag | actccatctc | aaaacaaaca | 780
| aacaaacaat | aagacaaaaa | aacttactct | cctttcaaac | cccttccaac | ctctactata | 840
| atgaaaatga | tggcagctga | ctcccttata | acagtaagtt | ttgaataaac | agcctttgat | 900
| taattctatt | ttgtttgcca | aagaaaataa | ttaaagtttg | gtaaaataaa | ataattaaaa | 960
| gaaaagaaa | tcatggacac | tctagaagaa | aacatttatt | tgagctttac | tgctgaaaaa | 1020

```
gaaaacatat tttaaaaagt aaccttgact gcacagcaaa agaaactatc aacaaagtaa      1080
gcagacaacc tacagaatgg aagaaaatat gcacaaacta tgtatctgac aaaggtctaa      1140
tattcagaat ctataaggaa cttaaatcaa caagcaaaaa acaaataacc ccatttatgg      1200
cctttgctta cttttgggc agtcctcaaa agaagacatc caagtggcaa acaatcatat       1260
gaaaaaatgc ttatcatcac taatcatcag agaaaagcaa gtcaaaacca cagtgaagta     1320
tcatcacaca ccagtcaaaa tggctattat taaaaataac agatgttggc agtgctgcag     1380
agaaaaggga ttgcttatgc actgttggtg agaatgtaaa ttcatttagc tactgtggaa     1440
agcaggagat ttctcaaaga actaaaaata tatatatcat tcaaaccaac aattccatta     1500
ctagatatat atccaaagga aaataaattg ttctatcaaa aagacacatg cacctgtatg     1560
ttcatcgcag tattattcgc aatagcaaat acatggaatc aaccaaggtg ttaatcaaca     1620
gaggagtgga taagaaaat gtggtacata tacaccatgg aatactatac agtcagaaga     1680
aagaatgaaa tcatggcctt tgcagcaaca tggatgcagc tagggaccat tatcctaagt     1740
aaactaatgc agaaacagaa aagcaaatgc cacatgttct cacttataag tgggagccaa     1800
gtgagtacac atggacatga aatggaaaca atagacactg gagactacaa gagaagggag     1860
ggggacaggg attgaaaaac tacctattgg gtactatgct cagtacttga gtgatgggtt     1920
caatcgtatg caaatttcag catcatgcaa tataccttg taacaaacct gcacatgtac      1980 caccctgaa tctaaaataa aagttgaaaa aacaaaaac aaaaaaccc cttggaatgg        2040 gaggagtctt ttcagaccaa acatgagacc cagaagacaa aaagtaaact gttaataagt     2100
taggctgcat agcaagccaa aatttttata tgaaacattt tttaaagtga aaagatagat     2160
aaattttcaa aacatataac aaagaattaa tttctttggt atacaatgag cttttaaaaa     2220
ttaataagaa taattcaatg agaggttgaa atgggtacaa atatagagtt aggtagaagc     2280
ataagaccta agtgtttgat agatcagtag ggtgactata gttcaagata atctattgta     2340
cctgtcaaaa tagctagaag agaacaattc aaatgttcct agcattaaaa aagataaata     2400
ttgccggtga tgaataccct aattactttt ttttttcca gacagagtct cgttctgtca     2460
cccaggctga agtgcaatgg cgcaatcttg gctcactgca acctccgcct cctgggttcc     2520
agtgattctc ctgtctcagc ctcccaagta gctgggatta caggggccca cagccatgcc     2580
tggctaattt ttgtattttt agcagagatg gggtttcacc atgttggtca gactggtctt     2640
gaactcctga tctcaggtga tacccccacc tcggcctccc aaagtgctgg gatgacaagc     2700
gttagtcact gtacccgacc tccttagatc tttacacatt atatgaatgt gtcaaattat     2760
tacatgtatc ccaaaaatat gtacattatg tgttaataaa aagatttca aaattaataa      2820 gaataattca ataaggaaaa tggacaaggg aagaaacaca caattccagg aaaaaataca    2880
aataatcaat aaatatatga tgcatttaat cacatataat agaagaaata caaataaaaa    2940
taaggcactt ttaacacaat ctattagaat accagatatt taaatttgac agaattgagt    3000
attggtgagg atatagagaa atgggcactc tcatcctaca ttgggagaaa tataaatcaa   3060
tactggattc ttgagattca gtttacaata agtacaattt aagatgtgca tatctcttta    3120
ccctgcaatt ccacttctag aaattttatcc taaatattta cttacaaatg agcaaagaca  3180
tatatgtaca gggatgttca gattttatg tcgggttttt gtacggacat agttttttt     3240 tttttttttt tttttttgan anggagtttc actntgtcgc ccaggctgga gtgcagnggc    3300
gtgatctcgg ntnactgnaa cctccgcctc ccaggttnaa gcaattntcc tgcctnagcc    3360
```

```
tcccaagtag ctgggattac aggcatgcnc caccacacct gggtagtttt tntatttta    3420 gnananacan agtttcacca tgttggccag gctggtctng aactcccggc ctcaggngat    3480
ttgcccgcca tggcctccca aagtganggg attacaggca tgtgccaccg agcctggcta    3540
tntggacata gttttagtt ctttgggata aatgcccaga agtgttactg ctatttaatc    3600
tttaaagaaa ctgccaaact acttttcaga gtggctgcat tattttccat tcccaccagc    3660
aaagtatgag taatctattt ttacgcattc ttcccaaat ttagtatttt cactttttt     3720 tttttttt tttgaggcag ggtcttgctc agttgcctag gctggagtgt agtggcacta    3780
tctcggctca ctgcaacccc tgcctcccag gcttaagcga tcctcacatc tcagcaacct    3840
gagtagctgg ggctacaggt gagtgctacc actcatgggt aattttttt gnattcttag    3900 tagaggtgga gttccgccat gttgcccagg ctggtctcaa actcctgacc tcaagcgatc    3960
cacctgcctc tgcctcccaa agtgctgggg ttacaggcgt gcaccactgt gcctggccat    4020
tctcactatt tttaattcaa aatagtttgt gttctctatt ctccacatct ttttgttctt    4080
tttaatcatc taaagtccat agtttgtatt aggattaact tactgttgta cattctctct    4140
ctctctctct ttttttttta atgagatgga gtttctctct ttttgccca ggccaagcgc    4200 aatggcacaa tctcggctca ctacaacctt tgcctcctgg gttcaagtga ttctcctgcc    4260
tcagcctccc aagtagctgg gattacaagt gcgtgccacc acacctggcc aattttgtat    4320
ttttagtaga gatgggggttt cacnatgttg gccgggctgg tctccaactc ctgacctcag    4380
ctgatctgcc tgcctcagcc tcccaaagtg ctgtaattat aggcataagc cactgtgcct    4440
ggcctagtgt tgtacattct gtgggttttg acaattgtat gcatctacat gtatgtacca    4500
ttatagtatt cctgttttta attttagcca ttctagtagg catgtagtga natctcatgg    4560 tgatttaat ttgcgtttcc gtaatggtta ataatgctga acatctttgc atgtgcttgt    4620
ttgtcatttg tgtttcctac ttggtgaaat aattgttcat gtcctttgtc catttctaa    4680 ttgaattttt ttttaccatt tagttttgag atttctttat acaatccaga tccaaatctc    4740
ttgtctcaaa tatggtttgc aaatacattc ctctaattca tatattgcct ttcctcctc    4800 ttaacaggat gtttcacaga gcaaaagttt tagttttgtt gaaatctcac ttttcatttt    4860
tttctttagt ggattgtgct tttgttgtca tatgtaagaa ctcttcactg ccctagatc    4920 cttgtattgg tttcctaaga ttgccatagc aaatcaccat gaacttagtg acaaaaagac    4980
agaaatttat tttcacttcc tactgtgggc agactagacg ttaattattt tcatgtatgc    5040
tcattcctat gacatctttc tgatataata attatagtta ttcttaagct tcacccttt    5100 ttctattagc tttgttacct tgggtgtcac tttttctttt ttgacattgt gacctatgcc    5160
agatcatgtc tgttagtact tagccctcca ttcacctctc cataatccct tttgtattcc    5220
tggagcttga tgcctgaaat gacacatcct acattccttt gccagatggg taccagttag    5280
cttgtgcaca tgggagacaa ccgtgaaaag actgaagtgg ggaagaaggg aggagctgtt    5340
gtgtttcagt gagcgccctt ggcagtggcg gtgacagtgg ctcctgttca gtggcaatgg    5400
tggagcagct agcaagacat gcagtaagcg caggctcata ggctatggtc caggagcagt    5460
caccgattcc tggtctttag gcaatatcat ctcccttgc ttctccagcc tttctaaaat    5520
tattgtacct tgactagtac aattttttag tattgggggt agtccaagga cacaggcttt    5580 aaaagtatg aattcagggt tgcctacctg cattgactgc gcttgaatca tgatggcctt    5640
ctggtcggtg gcaggaggtg acagtccaaa tcatgcagta gcaaaccaga tacttaaant    5700
atcatctgag atacttcaga agtacagccg tagccatacc ttcagaagag ataaagaaat    5760
```

-continued

```
gttctcctgg ccaggcgcgg tggctcacgc ctgtcattcc agcactttgg gaggccgagg    5820
gggtggatca cctgaggtcg ggagttcgag accagcctga ccaacatggg aaaccctgt     5880 ctctactaaa aatacaaaat tagccggggcg tggtggcaca tgcccataat cccagctact   5940
cgggaggcta aggcaggata atcgcttgaa cctgagaggc agaggttgcg gtgaactgag    6000
atcatgccat agtactccag cctgggcaac aagagtgaaa ctccatctca aaaaaaaaa    6060 aaagaaaaa aagataaaga aatgttctcc tttcttgcca tttctagggg tttggggatg    6120
gcgtacattg ctgcagggcg tgctcactct accatcttgc tccaatcttt atttttcaaa   6180
atacagtgct tatgcttggt tacttcagtt aagattattt ttaaaaatca taattaagca   6240
aaaatatatg gccatgctta aacatattta agataaatta agtgatttgg cctgtttcag   6300
tatcccaact cacatgctaa caggggcttg acctgtagct acggtaccct ggaggaaatg   6360
atcgcattta tttggttatt tcggtctaag tagtaatagt tctgtcctgg aaaaagact    6420 agcctcaagg catttctgat tgaatgtttt tcaattacag tctttaaacc agtatgccac   6480
agaactggct ctttccacat gacggccttt gtggtgggtg gcagattgcc ctgaggcctc   6540
gcaaaatgct aggctttcac aatgtcactg actgacagcc aggcccagca cagtcttggt   6600
gtgattgtgg ggctaaagtt attccacctt gtgcaatagc tacagccttc tctaaccagc   6660
tgcattctta taaagttaga agaaaatact ttttttttt tgagatggat tctcgctctg    6720
ttgcccaggc tggagtgcaa tggtgcgatc tcggctcgct gcaacctccg cctcctgggt   6780
tcaaacgatt ctcctccctc agaccccgga gtagctggga ttgcaggtgc ctgccaccac   6840
gcccggctaa cttttttgta ttttagtgg agacggggtt tcaccatctt cgtcaggctg    6900
gtctcagact cctgacctca agtgatctgc ccgcctcagc ctcccaaaat gctgggatta   6960
caggcatgag ctactgtgcc cggccaaaga aaatactttt tatgccagcc ctgaaactac   7020
cctgaagcac atacatcaac cttgaggcct cacactccat caagaggggt gaagggcatg   7080
aggaattaga aagcataggg attttttagtt agacagatct ggttcaaatc ctagacttgt   7140
gccttgaaca aattatttac cctcattgaa ctctagattc attatttgta aaatgaaaga   7200
caataatagt tatctccaaa ggaaagttga atatgatcat tcatttattc attaattcaa   7260
catttattat tgcctacttt gtgccaggtt ctattctagg aactaaggga tacaactttg   7320
aataggcaaa atctctgctc tcctgaagtt tacttttttt ttttttttt tgagacagag    7380 tttcactctt gtcacccagg ctggagcgca atggtgctct tggctcactg caacctccac   7440
ctcctgggtt caagtgattc tcttgtctca gcctcccaag tagctgggac tacaggtatg   7500
tgccaccacg cccggctatt tctgcatttt tagtagagat ggggtttcac catgttggcc   7560
agactggtct caaactcctg atctcaggtg atatgcctgt cttggccttc caaagtactg   7620
ggattacagg cctgagccac tgcacctgac ctgaagttta tgttctatta aatagcaaca   7680
gacagtaaca taaaccaaaa ataaatagga aaacaccata acaaaaatca aacagtgata   7740
taattgagag ttgcttctat ttcttttgt tgtcttcttg gttcaatcag cctgctaaac    7800
tatatggaac ctcattttca tgggccactt attttaagccg ggggaccttg aaagtctct    7860 catgtctctc atctcaacgg cctaatgtga cttctcttga aatatttgga cattagcagg   7920
aagctgaggc tttacatcag atctttactt taatggtgga cttgacttta ctggtagatt   7980
tttaggctct gtgtggactg tggagatgat atctggggg caggcagaca cttgccctgc    8040
ctctgtctga gaaaattctg ttttggatgt cttgttgaag ttggtgctgg catcctaagc   8100
```

-continued

```
ccttgctggg gtcgtaattt aattcatcag aatgtgtggc ttgcaagaac cggctcagat    8160
cctgcgcttc aaaacaaaa catgagcgtg ccaagaaagt ccaaggtgtt gaatgttgcc    8220
acttcaagcc taaactttct aggaacacct aagtgggtgg cagcttccag ttctccaggc   8280
tgcttctagg ccagagctgg gttccacaag agacagaata ggcatatata tgcttaagga    8340
actggaaaaa caggctctct ctctctcaca aacacacaca cacacatacc aaggtagctg    8400
tcaaaatgtt atccgaaatt ttggaaccaa aaaatcttga aagatggtat tccaatatca    8460
cattttatgt aagttttcta ttatattaga ttcaaattac gattcgaggc cacaagcttt    8520
aagaattcag ggcctttta acttgccaag ccccacacca ctccaggaac ttccccacac    8580
cccagttctc agaattcatg tgcaaggtct ttcctaaatc cagggtccag gtcagagagt    8640
ggaggatgtg ctctatttct tacctgattg cagaccctc tgacagtgct cccttctgaa     8700
gcactcactg tctgaacgta cacagtctca gacttaatca tgcacagtga gcaagactgt    8760
ggtgtgataa ttggcgtccc tgacttatta gggcaaatct atgggagggg gagacctcct    8820
ggaccactga gcaattaatt catttacatt aggaagtttc tccgtcagat gcaggaaaaa    8880
aatcttgttt tcctgctgtg gttttgactt ttgccccatc ttctgttgct gttgtaggag    8940
gcaaaataag ggtcaaggcc tggaaacaca agtgctttga ctgaagctcc acttggcttc    9000
cgaagcccaa gctgggttgt accaggttcc ctagggtgca ggctgtgggc aactgccagg    9060
gacatgtgcc tgcccaccgg cctctggccc tcactgagtt ggccaatggg aaatgacaat    9120
tgtgaggtgg ggactgcctg cccccgtgag taccaggctg ttgaggctgg gccatctcct    9180
cctcacttcc attctgactg cagtctgtgg ttctgattcc ataccagag               9229
```

<210> SEQ ID NO 4
<211> LENGTH: 1401
<212> TYPE: DNA
<213> ORGANISM: Homo sapiens

<400> SEQUENCE: 4

```
ccacttattt aagccggggg accttggaaa gtctctcatg tctctcatct caacggccta      60
atgtgacttc tcttgaaata tttggacatt agcaggaagc tgaggcttta catcagatct     120
ttactttaat ggtggacttg actttactgg tagatttta ggctctgtgt ggactgtgga    180
gatgatatct gggggcagg cagacacttg ccctgcctct gtctgagaaa attctgtttt     240
ggatgtcttg ttgaagttgg tgctggcatc ctaagccctt gctggggtcg taatttaatt    300
catcagaatg tgtggcttgc aagaaccggc tcagatcctg cgcttcaaaa acaaaacatg    360
agcgtgccaa gaaagtccaa ggtgttgaat gttgccactt caagcctaaa ctttctagga    420
acacctaagt gggtggcagc ttccagttct ccaggctgct ctaggccag agctgggttc    480 cacaagagac agaataggca tatatatgct taaggaactg gaaaacagg ctctctctct    540 ctcacaaaca cacacacaca cataccaagg tagctgtcaa aatgttatcc gaaattttgg    600
aaccaaaaaa tcttgaaaga tggtattcca atatcacatt ttatgtaagt tttctattat    660
attagattca aattacgatt cgaggccaca agctttaaga attcagggcc tttttaactt    720
gccaagcccc acaccactcc aggaacttcc cacacccca ttctcagaa ttcatgtgca     780 aggtctttcc taaatccagg gtccaggtca gagagtggag gatgtgctct atttcttacc    840
tgattgcaga ccctctgac agtgctccct tctgaagcac tcactgtctg aacgtacaca    900
gtctcagact taatcatgca cagtgagcaa gactgtggtg tgataattgg cgtccctgac    960
ttattagggc aaatctatgg gagggggaga cctcctggac cactgagcaa ttaattcatt   1020
```

-continued

```
tacattagga agtttctccg tcagatgcag gaaaaaaatc ttgttttcct gctgtggttt    1080
tgacttttgc cccatcttct gttgctgttg taggaggcaa ataagggtc aaggcctgga    1140 aacacaagtg ctttgactga agctccactt ggcttccgaa gcccaagctg ggttgtacca    1200
ggttccctag ggtgcaggct gtgggcaact gccagggaca tgtgcctgcc caccggcctc    1260
tggccctcac tgagttggcc aatgggaaat gacaattgtg aggtgggac tgcctgcccc     1320 cgtgagtacc aggctgttga ggctgggcca tctcctcctc acttccattc tgactgcagt    1380
ctgtggttct gattccatac c                                               1401
```

<210> SEQ ID NO 5
<211> LENGTH: 32
<212> TYPE: DNA
<213> ORGANISM: Homo sapiens

<400> SEQUENCE: 5

```
gaagcccaag ctgggttgta ccaggttccc ta                                    32
```

<210> SEQ ID NO 6
<211> LENGTH: 736
<212> TYPE: DNA
<213> ORGANISM: Homo sapiens

<400> SEQUENCE: 6

```
atgctgttgc tgggagctgt tctactgcta ttagctctgc ccggtcatga ccaggaaacc      60
acgactcaag ggcccggagt cctgcttccc ctgcccaagg gggcctgcac aggttggatg     120
gcgggcatcc cagggcatcc gggccataat ggggccccag gccgtgatgg cagagatggc     180
accccctggt agaagggtga gaaaggagat ccaggtctta ttggtcctaa gggagacatc     240
ggtgaaaccg gagtacccgg ggctgaaggt ccccgaggct ttccgggaat ccaaggcagg     300
aaaggagaac ctggagaagg tgcctatgta taccgctcag cattcagtgt gggattggag     360
acttacgtta ctatccccaa catgcccatt cgctttacca agatcttcta caatcagcaa     420
aaccactatg atggctccac tggtaaattc cactgcaaca ttcctgggct gtactacttt     480
gcctaccaca tcacagtcta tatgaaggat gtgaaggtca gcctcttcaa gaaggacaag     540
gctatgctct tcacctatga tcagtaccag gaaaataatg tggaccaggc ctccggctct     600
gtgctcctgc atctggaggt gggcgaccaa gtctggctcc aggtgtatgg ggaaggagag     660
cgtaatggac tctatgctga taatgacaat gactccacct tcacaggctt tcttctctac     720
catgacacca actgat                                                      736
```

<210> SEQ ID NO 7
<211> LENGTH: 244
<212> TYPE: PRT
<213> ORGANISM: Homo sapiens

<400> SEQUENCE: 7

```
Met Leu Leu Leu Gly Ala Val Leu Leu Leu Ala Leu Pro Gly His
1               5                   10                  15

Asp Gln Glu Thr Thr Thr Gln Gly Pro Gly Val Leu Leu Pro Leu Pro
            20                  25                  30

Lys Gly Ala Cys Thr Gly Trp Met Ala Gly Ile Pro Gly His Pro Gly
        35                  40                  45

His Asn Gly Ala Pro Gly Arg Asp Gly Arg Asp Gly Thr Pro Gly Glu
    50                  55                  60
```

-continued

```
Lys Gly Glu Lys Gly Asp Pro Gly Leu Ile Gly Pro Lys Gly Asp Ile
 65                  70                  75                  80
Gly Glu Thr Gly Val Pro Gly Ala Glu Gly Pro Arg Gly Phe Pro Gly
                 85                  90                  95
Ile Gln Gly Arg Lys Gly Glu Pro Gly Glu Gly Ala Tyr Val Tyr Arg
             100                 105                 110
Ser Ala Phe Ser Val Gly Leu Glu Thr Tyr Val Thr Ile Pro Asn Met
         115                 120                 125
Pro Ile Arg Phe Thr Lys Ile Phe Tyr Asn Gln Gln Asn His Tyr Asp
     130                 135                 140
Gly Ser Thr Gly Lys Phe His Cys Asn Ile Pro Gly Leu Tyr Tyr Phe
145                 150                 155                 160
Ala Tyr His Ile Thr Val Tyr Met Lys Asp Val Lys Val Ser Leu Phe
             165                 170                 175
Lys Lys Asp Lys Ala Met Leu Phe Thr Tyr Asp Gln Tyr Gln Glu Asn
             180                 185                 190
Asn Val Asp Gln Ala Ser Gly Ser Val Leu Leu His Leu Glu Val Gly
         195                 200                 205
Asp Gln Val Trp Leu Gln Val Tyr Gly Glu Gly Glu Arg Asn Gly Leu
     210                 215                 220
Tyr Ala Asp Asn Asp Asn Asp Ser Thr Phe Thr Gly Phe Leu Leu Tyr
225                 230                 235                 240
His Asp Thr Asn
```

ADIPONECTIN EXPRESSION-INDUCING AGENTS AND USES THEREOF

RELATED APPLICATIONS

This application is a National Phase Filing of International Patent Application No. PCT/JP2005/006357, filed Mar. 31, 2005, which claims priority to U.S. Provisional Patent Application No. 60/557,708, filed Mar. 31, 2004, the disclosures of each of which are hereby incorporated by reference.

TECHNICAL FIELD

The present invention relates to adiponectin expression-inducing agents, and particularly relates to pharmaceutical agents that can induce adiponectin expression through KLF9, and preventive and/or therapeutic agents for metabolic diseases or heart diseases using such agents. Furthermore, the present invention relates to substances that can induce adiponectin expression, methods of screening for preventive and/or therapeutic agents for metabolic diseases or heart diseases that use such substances, and cells used in the screening methods.

BACKGROUND ART

Obesity is defined as an increase in the amount of adipose tissue, and is a high risk factor in the development of diabetes, hyperlipidemia, and cardiovascular and metabolic diseases such as coronary heart disease (Non-Patent Documents 1 and 2). However, molecular mechanisms that can explain the relationship between obesity and these diseases have not been elucidated. Adipose tissue itself functions as a tissue that carries out triglyceride (TG) storage and free fatty acid (FFA)/glycerol release depending on the changing energy requirements (Non-Patent Document 1). Adipose tissue is an important endocrine organ that secretes a large number of biologically active substances called "adipokines" such as FFA (Non-Patent Document 3), adipsin (Non-Patent Document 4), tumor necrosis factor α (Non-Patent Document 5), leptin (Non-Patent Document 6), plasminogen activator inhibitor 1 (Non-Patent Document 7), and resistin (Non-Patent Document 8), and controls energy homeostasis in various ways.

Adiponectin or Acrp30 (Non-Patent Document 9 to 12) is an adipose tissue-derived hormone that has several biological functions. The level of plasma adiponectin is decreased in obesity and in insulin-resistance and type II diabetes (Non-Patent Document 13). Experiments using mice have confirmed that administration of adiponectin decreases the blood glucose level and improves insulin resistance (Non-Patent Documents 14 to 16). On the other hand, there are reports that when adiponectin is knocked out in mice, insulin resistance and morbid conditions of diabetes are observed (Non-Patent Documents 17 and 18).

The insulin sensitivity-inducing activity of adiponectin is presumed to be induced by increase in fatty acid oxidation through PPARα activation (Non-Patent Documents 19 and 20), or acutely via AMP kinase (Non-Patent Documents 21 and 22). In endothelial cells (human aortic endothelial cells: HAEC) and macrophages, adiponectin may have antiatherogenic properties which are similar to anti-inflammatory effects (Non-Patent Documents 23 and 24). It was shown that when adiponectin is highly expressed in apoE knockout mice, the expression of molecules related to inflammation decreases, and along with this, atherosclerosis is improved (Non-Patent Documents 19 and 25). Neointimal formation was increased in adiponectin knockout mice (Non-Patent Documents 17 and 26).

Recently, the cloning of cDNAs encoding adiponectin receptor (AdipoR) 1 and 2 was reported (Non-Patent Document 27 and Patent Document 1). AdipoR1 is expressed abundantly in skeletal muscle, whereas AdipoR2 is expressed mainly in the liver. AdipoR1 and R2 comprise seven transmembrane domains (Non-Patent Document 27), but they are presumed to be distinguishable from G protein-coupled receptors, both structurally and functionally (Non-Patent Documents 28 to 30). AdipoR1 and R2 function as receptors for globular and full-length adiponectin, and induce AMPK activation (Non-Patent Documents 21 and 22), PPARα ligand activation (Non-Patent Documents 19 and 20), and increased fatty acid oxidation and glucose uptake due to adiponectin (Non-Patent Document 27).

[Patent Document 1] WO2004/061108
[Non-Patent Document 1] Spiegelman, B. M. & Flier, J. S., Cell 87, 377-389 (1996).
[Non-Patent Document 2] Friedman, J. M., Nature 404, 632-634 (2000).
[Non-Patent Document 3] White, R. T. et al., J. Biol. Chem. 267, 9210-9213 (1992).
[Non-Patent Document 4] Hotamisligil, G. S. et. al., Science 259, 87-91, (1993).
[Non-Patent Document 5] Zhang, Y. et al., Nature 372, 425-432, (1994).
[Non-Patent Document 6] Shulman, G. I., J. Clin. Invest. 106, 171-176 (2000).
[Non-Patent Document 7] Shimomura, I. et al., Nat. Med. 2, 800-803 (1996).
[Non-Patent Document 8] Steppan, C. M. et al., Nature 409, 307-312 (2001).
[Non-Patent Document 9] Scherer, P. E. et al., J. Biol. Chem. 270, 26746-26749 (1995).
[Non-Patent Document 10] Hu, E., Liang, P. & Spiegelman, B. M., J. Biol. Chem. 271, 10697-10703 (1996).
[Non-Patent Document 11] Maeda, K. et al. Biochem. Biophys. Res. Commun. 221, 286-296 (1996).
[Non-Patent Document 12] Nakano, Y, et al., J. Biochem. (Tokyo) 120, 802-812 (1996).
[Non-Patent Document 13] Hotta, K. et al., Arterioscler. Thromb. Vasc. Biol. 20, 1595-1599, 2000.
[Non-Patent Document 14] Fruebis, J. et al., Proc. Natl. Acad. Sci. USA. 98, 2005-2010 (2001).
[Non-Patent Document 15] Yamauchi, T. et al., Nat. Med. 7, 941-946 (2001).
[Non-Patent Document 16] Berg, A. H. et al., Nat. Med. 7, 947-953 (2001).
[Non-Patent Document 17] Kubota, N. et al., J. Biol. Chem. 277, 25863-25866 (2002).
[Non-Patent Document 18] Maeda, N. et al., Nat. Med. 8, 731-737 (2002).
[Non-Patent Document 19] Kersten, S. et al., Nature 405, 421-424 (2000).
[Non-Patent Document 20] Yamauchi, T. et al., J. Biol. Chem. 278, 2461-2468 (2003).
[Non-Patent Document 21] Yamauchi, T. et al., Nat. Med. 8, 1288-1295 (2002).
[Non-Patent Document 22] Tomas, E. et al., Proc. Natl. Acad. Sci. USA. 99, 16309-16313 (2002).
[Non-Patent Document 23] Ouchi, N. et al., Circulation 103, 1057-1063 (2001).
[Non-Patent Document 24] Yokota, T. et al., Blood 96, 1723-1732 (2000).

[Non-Patent Document 25] Okamoto, Y et al., Circulation 106, 2767-2770 (2002).

[Non-Patent Document 26] Matsuda, M. et al., J. Biol. Chem. 277, 37487-37491 (2002).

[Non-Patent Document 27] Yamauchi, T. et al., Nature 423, 762-769 (2003).

[Non-Patent Document 28] Wess, J., FASEB. J. 11, 346-354 (1997).

[Non-Patent Document 29] Yokomizo, T. et al., Nature 387, 620-624 (1997).

[Non-Patent Document 30] Scheer, A. et al., EMBO. J. 15, 3566-3578 (1996).

DISCLOSURE OF THE INVENTION

Decrease in adiponectin production observed in obesity may be a determining factor of the onset of obesity-related diseases such as insulin resistance, diabetes, and cardiovascular diseases. However, the underlying molecular determinants have not yet been elucidated. Therefore, an objective of the present invention is first, to elucidate the functional mechanism of adipocyte hypertrophy-dependent suppression of adiponectin production; second, to identify factors that can increase the expression of adiponectin gene; third, to provide adiponectin expression-inducing agents, and therapeutic agents using these agents for obesity and obesity-related diseases such as cardiovascular diseases and metabolic diseases; and fourth, to provide methods for searching adiponectin expression-inducing agents.

As described above, adiponectin/Acrp30 is a hormone secreted by adipocytes, and functions as an antidiabetic and antiatherogenic adipokine. Transcription of adiponectin/Acrp30 is decreased in obese adipose tissue, and this decrease is involved in the development of insulin resistance in obesity. To elucidate the mechanism responsible for transcriptional regulation of the adiponectin gene, the present inventors produced a hypertrophic adipocyte model for identifying the position of the adiponectin gene promoter region. Using this cell model, promoter activity of a region comprising −1367 base pair (bp) to +35 bp of the promoter equipped with a luciferase gene as a reporter gene was examined. High-level luciferase activity was detected in adipocytes that had been introduced with a plasmid comprising only 156 bp of the adiponectin promoter. On the other hand, in hypertrophic adipocytes, only the reporter gene equipped with 217 bp of the upstream regulatory region of the adiponectin gene showed suppression of the expression.

Electrophoretic mobility shift assay (EMSA) showed that a 32-bp fragment of position −188 to position −157 from the transcription start site of the adiponectin gene binds to proteins in nuclear extracts prepared separately from adipocytes and adipose tissue. Substances that decrease the electrophoretic mobility of the 32-bp element were found mostly in the nuclear extracts prepared from small adipocytes, as compared with those prepared from large adipocytes. Similarly, more of such substances were found in the nuclear extracts prepared from adipose tissues of lean mice than those from obese mice. A nuclear factor that binds to the 32-bp fragment was identified using the yeast one-hybrid screening method. Six positive factors obtained from the one-hybrid screening were further analyzed by EMSA and chromatin immunoprecipitation assay, and Kruppel-like factor 9 (hereinafter abbreviated as "KLF9") was identified. KLF9 binds to the above-mentioned element, and the binding level correlates with the in vitro and in vivo KLF9 expression levels. In addition, cotransfection experiments showed that transient overexpression of KLF9 enhances adiponectin promoter activity specifically and dose-dependently. In vitro suppression of KLF9 expression by siRNA and KLF9 overexpression as well as in vivo KLF9 knockout cause changes in the endogenous adiponectin mRNA level. This confirmed that transcriptional regulation of adiponectin is carried out by KLF9. These results suggest that if supplemented to swollen hypertrophic adipocytes, KLF9 can be used as a preventive and/or therapeutic agent for obesity or obesity-related diseases such as metabolic diseases including insulin resistance and type II diabetes, and cardiovascular diseases. These results also indicate that KLF9 is important as a target for drug discovery against the above-mentioned diseases. The present invention is based on these findings and specifically relates to:

[1] an adiponectin expression-inducing agent, which comprises the protein of (1) or (2):

(1) a protein comprising the amino acid sequence of SEQ ID NO: 2, or (2) a protein comprising an amino acid sequence with one or more amino acid deletions, substitutions, additions, or insertions in the amino acid sequence of SEQ ID NO: 2;

[2] an adiponectin expression-inducing agent, which comprises the DNA of (1) or (2), or a vector carrying said DNA:

(1) a DNA comprising the nucleotide sequence of SEQ ID NO: 1, or (2) a DNA that hybridizes under stringent conditions with the nucleotide sequence of SEQ ID NO: 1;

[3] a preventive or therapeutic pharmaceutical composition for a metabolic disease or heart disease, wherein the composition comprises the adiponectin expression-inducing agent of [1] or [2] as an active ingredient;

[4] a cell for screening for an adiponectin expression-inducing substance, wherein the cell carries a reporter gene that is quipped with at least an enhancer element comprising:

(1) a DNA comprising the nucleotide sequence of SEQ ID NO: 5, or (2) a DNA comprising a nucleotide sequence with one or more nucleotide deletions, additions, substitutions, or insertions in the nucleotide sequence of SEQ ID NO: 5;

[5] the cell of [4], which further carries a KLF9-encoding DNA;

[6] the cell of [4] or [5], which is an adipocyte;

[7] the cell of [4] or [5], which is a hypertrophic adipocyte;

[8] a method of screening for an adiponectin expression-inducing substance, wherein the method comprises the steps of:

(1) reacting the cell of [4] with a test substance, (2) detecting expression of a reporter gene, and (3) selecting a test substance that yields a higher reporter gene expression in the cell reacted with the test substance than in the cell that has not reacted with the test substance;

[9] a method of screening for a substance that can induce adiponectin expression, wherein the method comprises the steps of:

(1) reacting the cell of [5] with a test substance, (2) detecting expression of a reporter gene, and (3) selecting a test substance that yields a higher reporter gene expression in the cell treated with the test substance than in the cell that has not reacted with the test substance;

[10] a method of screening for a preventive or therapeutic pharmaceutical agent for obesity or an obesity-related disease, wherein the method comprises the steps of:

(1) reacting the cell of [4] with a test substance, (2) detecting expression of a reporter gene, and (3) selecting a test substance that yields a higher reporter gene expression in the cell reacted with the test substance than in the cell that has not reacted with the test substance; and

[11] a method of screening for a preventive or therapeutic pharmaceutical agent for obesity or an obesity-related disease, wherein the method comprises the steps of:
(1) reacting the cell of [5] with a test substance,
(2) detecting expression of a reporter gene, and
(3) selecting a test substance that yields a higher reporter gene expression in the cell reacted with the test substance than in the cell that has not reacted with the test substance.

The rate of increase in the reporter gene expression, when 3T3L1 adipocytes (day 19) carrying PDGF-tk-luc or 32 bp-tk-luc as a reporter are introduced with mKLF5/pcDNA3.1 or mKLF9/pcDNA3.1, is indicated as an activity relative to the case without introduction. (d) Results of measuring the expression level of KLF9 when the KLF9 gene is stably introduced into 3T3L1 adipocytes (day 19) using retroviral vectors. The vertical axis "mKLF9/36B4" refers to KLF9 mRNA expression ratio corrected using the 36B4 mRNA expression level. (f) Results of measuring the expression level of adiponectin when the KLF9 gene was stably introduced into 3T3L1 adipocytes (day 19) using retroviral vectors. (e) A photograph showing the result of preparing a nuclear protein extract from 3T3L1 adipocytes (day 19) introduced with KLF9 using a retrovirus, and subjecting it to EMSA analysis using the adiponectin promoter (−188/−157) sequence as a $^{32}$P-labeled probe. Each of the bars in the figure shows mean±SE (n=5 to 7). KLF9 increased activities of the enhancer and adiponectin promoter, amount of the 32-bp binding protein, and expression of adiponectin.

FIG. 7 presents a photograph and a diagram showing results of analyzing the effect of KLF9 knockdown by siRNA on adiponectin expression. (a) KLF3, KLF9, and adiponectin mRNA levels 72 hours after introducing a KLF9 siRNA into 3T3L1 adipocytes (day 10). Each of the results was shown as a relative ratio by making the activity without siRNA introduction as 100%. (b) A photograph showing results of preparing a nuclear protein extract from cells 72 hours or 96 hours after introducing siRNA into 3T3L1 adipocytes (day 10), and subjecting this to EMSA analysis using the adiponectin promoter (−188/−157) sequence as a $^{32}$P-labeled probe. Suppression of KLF9 expression by siRNA decreased the amount of the 32-bp binding protein and adiponectin expression in vitro.

Figure 8:
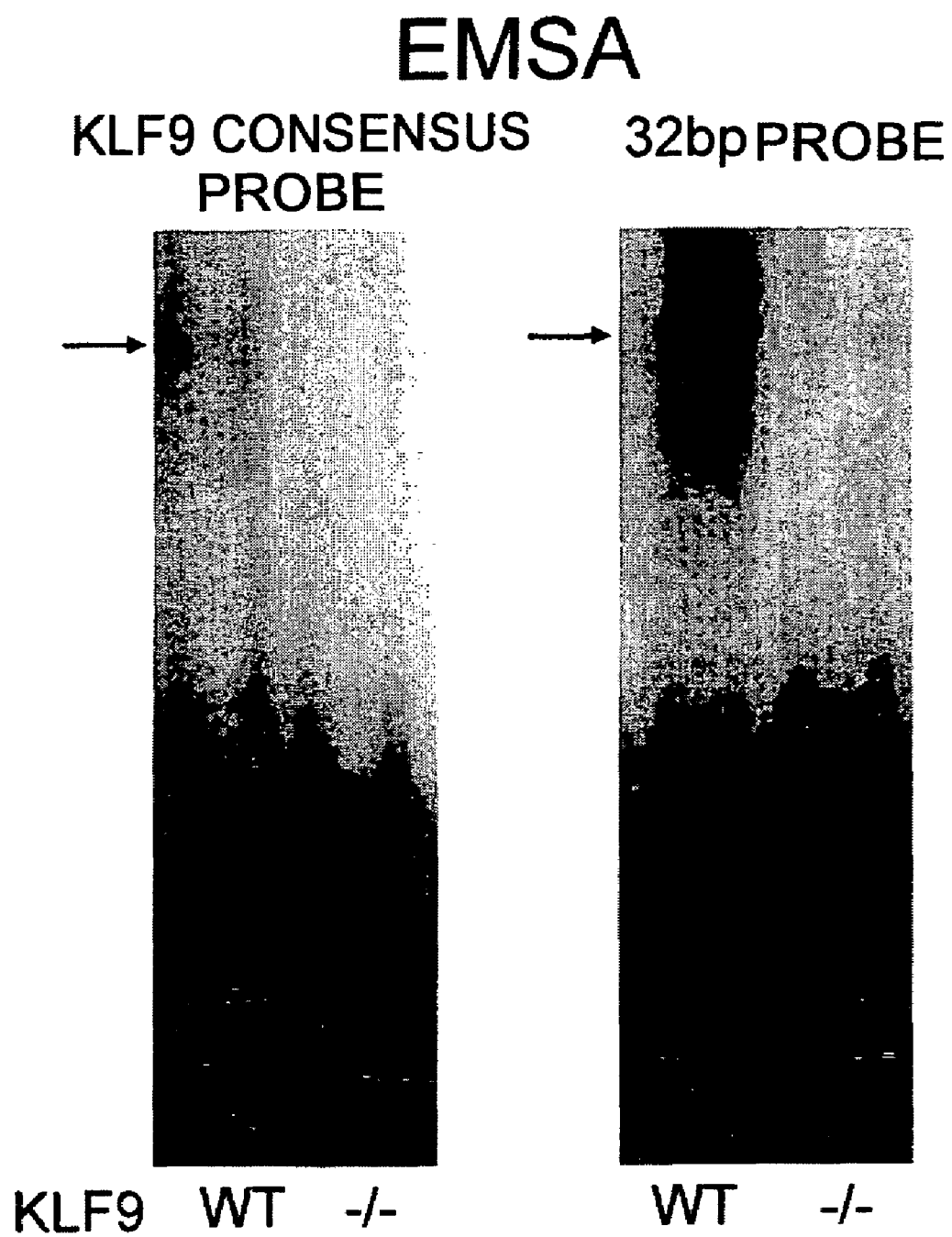

FIG. 8 is a photograph showing results of preparing a nuclear protein extract from WAT of KLF9 knockout mice or control wildtype littermates and then performing EMSA analysis using the KLF9 consensus sequence (BTE) or the adiponectin promoter (−188/−157) sequence as a $^{32}$P-labeled probe. KLF9 knockout eliminated the 32-bp binding protein, in addition to the KLF9 protein.

Figure 9:
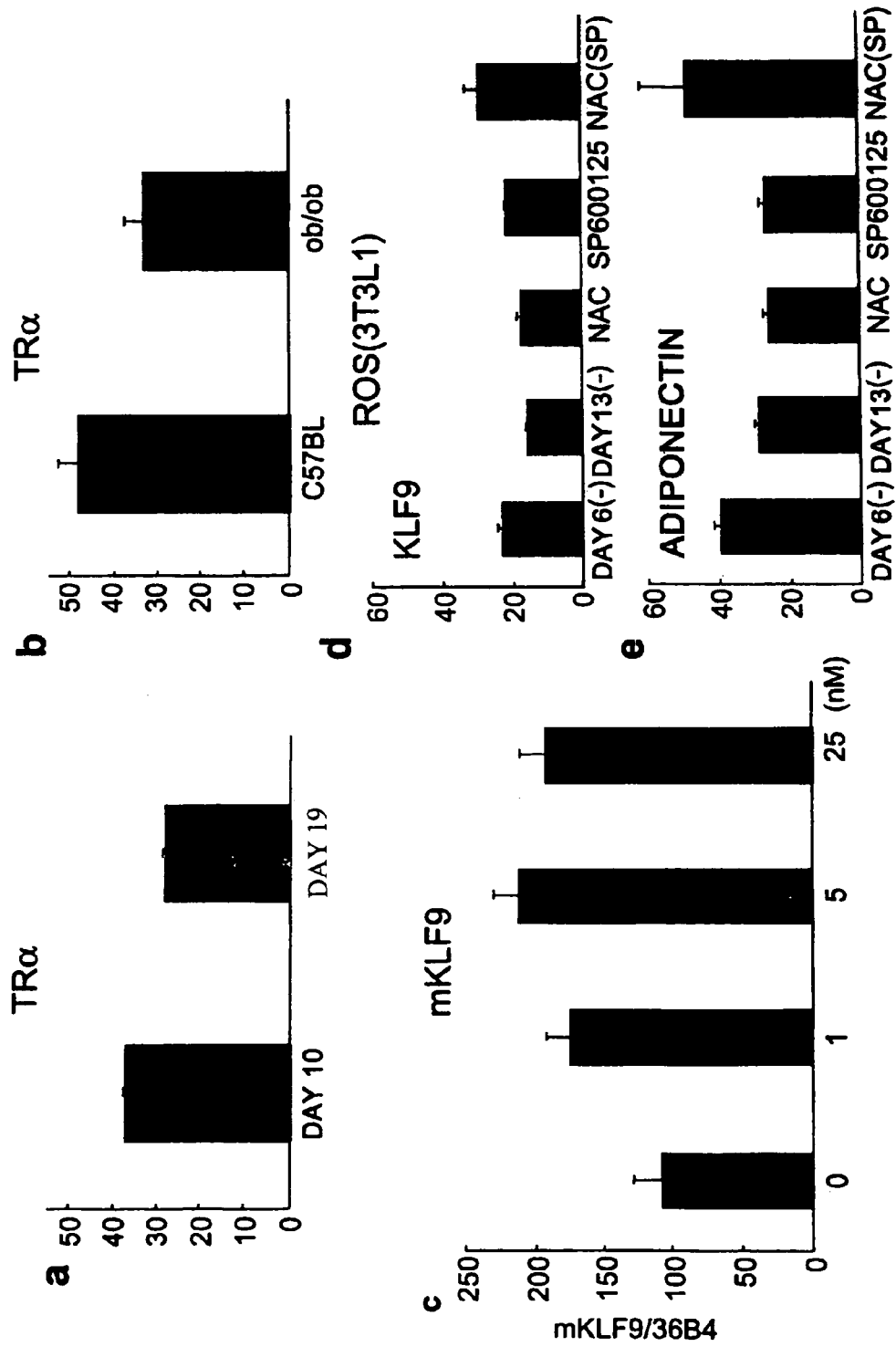

FIG. 9 shows the mechanism by which adipocyte hypertrophy regulates KLF9 expression in adipocytes. (a) The mRNA expression level of thyroid hormone receptor α (TRα) in 3T3L1 adipocytes (day 10 or day 19). (b) TRα mRNA expression levels in lean C57BL mice and obese ob/ob mice. (c) KLF9 mRNA expression levels after T3 treatment at concentrations indicated in the figure are shown as ratios relative to the 36B4 mRNA expression level. (d and e) The mRNA expression levels of KLF9 or adiponectin in 3T3L1 adipocytes (days 6 and 13), and in 3T3L1 adipocytes (day 19) treated with N-acetyl cysteine (NAC) (20 mM) which is an antioxidant, SP 600125 which is a JNK inhibitor, or NAC (SP). In the figure, NAC(SP) refers to the group treated with NAC and SP600125.

Figure 10:
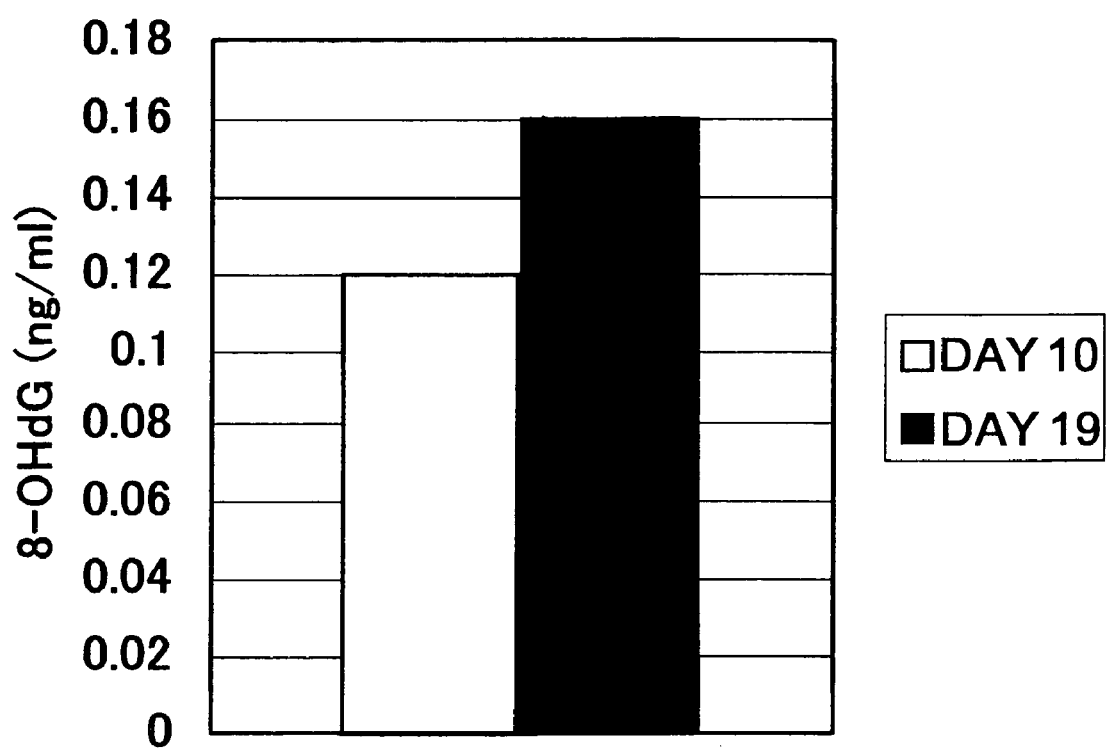

FIG. 10 shows oxidative stress increases along with adipocyte hypertrophy.

FIG. 11 shows anti-oxidative activity decreases along with adipocyte hypertrophy. Each of the bars shows mean±SE (n=6) (**: P<0.01; relative to untreated cells).

BEST MODE FOR CARRYING OUT THE INVENTION

Hereinafter, the present invention will be described with reference to embodiments. First, the present invention provides adiponectin expression-inducing agents. The present inventors discovered that KLF9 induces the expression of adiponectin. More specifically, the adiponectin expression-inducing agents of the present invention comprise as a constituent, the KLF9 protein, or a DNA that can express KLF9, or such.

KLF9 is one of the proteins that belong to a superfamily called "Kruppel-like zinc finger protein". A specific example of an amino acid sequence of KLF9 is shown in SEQ ID NO: 2, but KLF9 of the present invention is not limited thereto. Among these proteins, there are heterologous homologs and mutants that comprise similar sequences and have the same function. In addition, by making appropriate artificial modifications to the amino acid sequence of SEQ ID NO: 2, mutants having the same function may be obtained. Therefore, KLF9 of the present invention also encompasses proteins that comprise an amino acid sequence with one or more amino acid deletions, substitutions, or additions in the amino acid sequence of SEQ ID NO: 2, and have the adiponectin gene-inducing activity.

KLF9 can be obtained from cells and tissues of humans, mice, and such. For example, even small adipocytes highly express KLF9; therefore, adipocytes and adipose tissues in which differentiation has not progressed can be used as materials for isolating KLF9. KLF9 can also be obtained by simply linking the DNA of SEQ ID NO: 1 to an expression vector, and expressing it in a cell-based system or cell-free system.

Meanwhile, artificial amino acid substitution is an example of a method for obtaining a functionally equivalent protein of KLF9 comprising the amino acid sequence of SEQ ID NO: 2. Substitution between amino acids with similar properties is likely to maintain protein activity. Amino acid groups that are suitable for conservative substitution include basic amino acids (for example, lysine, arginine, and histidine), acidic amino acids (for example, aspartic acid and glutamic acid), uncharged polar amino acids (for example, glycine, asparagine, glutamine, serine, threonine, tyrosine, and cysteine), non-polar amino acids (for example, alanine, valine, leucine, isoleucine, proline, phenylalanine, methionine, and tryptophan), β-branched amino acids (for example, threonine, valine, and isoleucine), and aromatic amino acids (for example, tyrosine, phenylalanine, tryptophan, and histidine). On the other hand, nonconservative substitution of amino acid sequences may also be effective in certain cases. For example, nonconservative substitution can add modifications such as those that increase the adiponetin expression-inducing activity of the KLF9 protein. Such modified KLF9 proteins are also comprised in the present invention.

Another example of a method for obtaining proteins that are functionally equivalent to KLF9 is a method of cloning DNAs that are similar to the DNA of SEQ ID NO: 2 by hybridization, and obtaining proteins from these DNAs. More specifically, a KLF9-encoding DNA shown in SEQ ID NO: 1 or a fragment thereof is used as a probe for isolating DNAs that hybridize to the probe. DNAs with a highly homologous nucleotide sequence are selected by performing hybridization under stringent conditions, and as a result, functionally equivalent proteins of KLF9 are very likely to be isolated. Highly homologous nucleotide sequences demonstrate, for example, an identity of 70% or more, and preferably 90% or more.

The above-mentioned "stringent conditions" refers to conditions such as hybridization in 6×SSC and 40% formamide at 25° C., and washing in 1×SSC at 55° C. Stringency is influenced by conditions such as salt concentration, formamide concentration, or temperature; however, it is obvious that those skilled in the art can set these conditions to achieve the required stringency.

Mouse-derived KLF9 such as that comprising the amino acid sequence of SEQ ID NO: 2, and KLF9 homologs encoded by polynucleotides that can be obtained by using hybridization from animal species other than mice, that is, humans, rats, rabbits, pigs, and goats may constitute functionally equivalent proteins.

In addition to the above-mentioned methods, examples of methods for obtaining proteins that are functionally equivalent to KLF9 include methods that modify the DNA of SEQ ID NO: 1 and then synthesize proteins based on the modified DNAs. Proteins obtained by artificially modifying mouse KLF9 (SEQ ID NO: 2), and proteins encoded by polynucleotides isolated using the above-mentioned hybridization techniques and such are usually highly homologous to human KLF9 at the amino acid level. "Highly homologous" refers to sequence identity of at least 30% or more, preferably 50% or more, and more preferably 80% or more (for example, 95% or more). Nucleotide sequence identity and amino acid sequence identity can be determined using Internet homology search websites homology searches, such as FASTA, BLAST, PSI-BLAST, and SSEARCH can be used through the DNA Data Bank of Japan (DDBJ) [for example, the homology search (Search and Analysis) page on DDBJ website; http://www.ddbj.nig.ac.ip/search/Welcome-j.html]. BLAST searches can be performed with National Center for Biotechnology Information (NCBI) (for example, the BLAST page on the NCBI website; http://www.ncbi.nlm.nih.gov/BLAST/; Altschul, S. F. et al., J. Mol. Biol., 1990, 215(3): 403-10; Altschul, S. F. & Gish, W., Meth. Enzymol., 1996, 266: 460-480; Altschul, S. F. et al., Nucleic Acids Res., 1997, 25:3389-3402)].

Whether a functionally equivalent protein of KLF9 indeed has a function equivalent to that of KLF9 of SEQ ID NO: 2, or more specifically, adiponectin expression-inducing activity, can be confirmed by luciferase analysis described in the Examples herein.

Another component of the adiponectin expression-inducing agents of the present invention is a KLF9-encoding DNA or a vector carrying such DNA. An example of a KLF9-encoding DNA is a DNA comprising the nucleotide sequence of SEQ ID NO: 1. As in proteins, homologs and modified forms that have identical functions and comprise similar nucleotide sequences also exist in DNAs, and they can be obtained by artificially modifying the nucleotide sequence of SEQ ID NO: 1, or by cloning mutants having identical functions. Such DNAs comprising a sequence similar to that of SEQ ID NO: 1 can be defined, for example, as DNAs that hybridize under stringent conditions with the nucleotide sequence of SEQ ID NO: 1.

As described above, "DNAs that hybridize under stringent conditions" are DNAs that can hybridize with a DNA encoding KLF9 of SEQ ID NO: 1 by using the DNA or a fragment thereof as a probe. An example of the stringent conditions is conditions such as hybridization in 6×SSC and 40% formamide at 25° C., and washing in 1×SSC at 55° C., as described above, but they are not limited thereto.

KLF9-encoding DNAs may be used in the form of fragments, or in the form of vectors carrying them. The vectors are appropriately selected depending on the purpose. For example, when the objective is to induce expression of the adiponectin gene in human cells and tissues, vectors that can function in mammalian cells such as human cells, for example, retroviral vectors, adenoviral vectors, adeno-associated virus vectors, lentiviral vectors, pcDNAI, and pcDNAI/Amp (Invitrogen), are available.

The adiponectin expression-inducing agents of the present invention can be used for: (1) inducing expression of an endogenous or exogenous adiponectin gene in laboratory animals, (2) inducing expression of an endogenous or exogenous adiponectin gene in cultured cells, (3) inducing expression of an adiponectin gene in cell-free systems, and such.

In the cases of (1) and (2), adiponectin expression-inducing agents, which comprise a KLF9-encoding DNA carried by a vector as a component, are preferably used. Gene transfer into cells, tissues, and such can be carried out by administering viral vectors or by using conventional gene transfer techniques (electroporation, lipofection, calcium phosphate precipitation, and such). In the case of (3), the adiponectin expression-inducing agents may comprise either a vector carrying the DNA or the KLF9 protein as a component.

Since the adiponectin expression-inducing agents of the present invention can induce expression of adiponectin in laboratory animals, cultured cells, and also cell-free systems, they will become effective pharmaceutical agents for functional analysis of adiponectin. Adiponectin is an important factor involved in obesity or obesity-related diseases including metabolic diseases such as diabetes, and cardiovascular diseases such as arteriosclerosis. Therefore, the instant pharmaceutical agents should contribute greatly to studies of such diseases.

Secondly, the present invention relates to preventive and/or therapeutic pharmaceutical Compositions for obesity or obesity-related diseases, in which the compositions comprise the adiponectin expression-inducing agents as an active ingredient. As described above, adiponectin is an important factor involved in obesity or obesity-related diseases including metabolic diseases such as type II diabetes and insulin resistance, and cardiovascular diseases such as arteriosclerosis. In many of these diseases, hypoadiponectinemia is observed. Therefore, by using the adiponectin expression-inducing agents as an active ingredient and appropriately mixing it with a pharmaceutically acceptable carrier, the resulting compositions can be applied as a pharmaceutical composition for treating obesity or obesity-related diseases.

Diseases targeted by the pharmaceutical compositions of the present invention are obesity or obesity-related diseases such as metabolic diseases and heart diseases. More specifically, they are metabolic diseases such as insulin resistance, diabetes, and hyperlipidemia, and cardiovascular diseases such as arteriosclerosis, hypertension, and fatty liver. Even more specifically, among these diseases, the pharmaceutical compositions of the present invention are effective especially in cases accompanied by hypoadiponectinemia, or cases that may cause hypoadiponectinemia. Prevention, treatment, alleviation of pathology, and such of the above-mentioned diseases can be achieved by using an adiponectin expression-inducing agent comprised in the pharmaceutical compositions of the present invention to improve hypoadiponectinemia which causes these diseases or develops along with these diseases.

The adiponectin expression-inducing agents are as described above. "Pharmaceutically acceptable carriers" refers to excipients, diluents, expanders, disintegrators, stabilizers, preservatives, buffers, or other additives. Oral or parenteral formulations can be prepared using one or more of such carriers. The dosage of the pharmaceutical compositions of the present invention can be appropriately adjusted according to the target diseases and pathologies, and in general, they are usually 1 µg to 20 g per kg weight, and more generally 10 µg to 500 mg per kg weight. In the case of injections, the dosage is roughly one tenth to one hundredth of the oral dosage.

Thirdly, the present invention provides cells to be used in screening for adiponectin expression-inducing agents. The present inventors have identified an element to which KLF9 binds in the regulatory region of an adiponectin gene. Expression of adiponectin is enhanced when KLF9 binds to this element. Therefore, by searching substances having activities similar to that of KLF9, one can screen for adiponectin expression-inducing factors that can replace KLF9. These factors may be proteins like KLF9, but they are preferably low molecular weight compounds. If they are low molecular weight compounds, they are very likely to be used as lead compounds for drug discovery without modification.

The first embodiment of the cells of the present invention is cells carrying a reporter gene that is equipped with an element (hereinafter referred to as "KLF9-binding element") to which KLF9 can bind at least in the upstream region. More specifically, in the cells of the first embodiment, a KLF9-binding element, which is an enhancer element (cis factor) that promotes the KLF-9 mediated adiponectin gene expression, is located upstream of the reporter gene.

An example of a KLF9-binding element is preferably the nucleotide sequence of SEQ ID NO: 5, which corresponds to positions −188 to −157 in the upstream of the adiponectin gene. However, a KLF9-binding element is not limited to this sequence, and it includes the full length of the regulatory region of an adiponectin gene (SEQ ID NO: 3) comprising the nucleotide sequence of SEQ ID NO: 5, or a part thereof (for example, SEQ ID NO: 4), which is located upstream of the reporter gene. Furthermore, the nucleotide sequence of SEQ ID NO: 5 may be modified as long as the modified sequence is a sequence to which KLF9 can bind and which maintains the activity of inducing KLF9-mediated adiponectin gene expression. More specifically, a modified sequence of the nucleotide sequence of SEQ ID NO: 5 can be defined as a nucleotide sequence with one or more nucleotide deletions, additions, substitutions, or insertions in the nucleotide sequence of SEQ ID NO: 5. Such modifications of the nucleotide sequence of SEQ ID NO: 5 can be performed using point mutation techniques.

Reporter genes are not particularly limited so long as they are genes whose expression can be confirmed, and this term will be used herein in a broader sense than its ordinary usage. More specifically, "reporter genes" as used herein includes the adiponectin gene itself in addition to the conventional reporter genes (marker genes) such as genes whose expression can be detected using luminescence as an index (for example, luciferase gene, GFP gene, and YFP gene), genes whose expression can be detected using enzyme activity as an index (for example, β-galactosidase gene), and genes whose expression can be detected using agent sensitivity as an index (for example, neomycin-resistance gene and hygromycin-resistance gene). Herein, unless otherwise stated, the term "reporter gene" is understood in a broad sense.

More specifically, an adiponectin gene equipped with an intrinsic regulatory region (for example, SEQ ID NO: 3), such as SEQ ID NO: 6, can be used as a "reporter gene equipped with a KLF9-binding element in the upstream region". The adiponectin gene in this construct may be substituted with a conventional reporter gene such as those described above. Furthermore, in such constructs, parts other than the KLF9-binding element of the regulatory region may be deleted so that only the KLF9-binding element (for example SEQ ID NO: 5) remains. Such constructs can also be made based on a plasmid carrying a conventional reporter gene, by replacing the upstream sequence of the reporter gene with the regulatory region of the adiponectin gene, or by inserting a KLF9-binding element in the upstream of the conventional reporter gene. When using the adiponectin gene as a reporter gene, the adiponectin gene may be a cellular endogenous gene or an exogenously introduced gene.

The second embodiment of the cells of the present invention is cells of the first embodiment carrying a KLF9-encoding DNA additionally. The cells of the second embodiment, which are cells of the first embodiment additionally carrying the KLF9 gene, are useful in screening for substances that can induce expression of the adiponectin gene through induction of KLF9 gene expression. The present inventors have discovered that decrease in the KLF9 gene expression, particularly at the transcriptional level, is correlated with a decrease in the adiponectin expression during adipocyte hypertrophy. Therefore, in addition to the utility of the cells of the first embodiment, cells of the second embodiment are useful in searching for substances that inhibit substances which suppress the KLF9 gene expression in large or hypertrophic adipocytes.

"A KLF9-encoding DNA" is the same as the KLF9-encoding DNA mentioned above in the description of adiponectin expression-inducing agents, and the scope of the meaning of this phrase is also the same. Specifically, an example of a KLF9-encoding DNA is a DNA comprising the nucleotide sequence of SEQ ID NO: 1. Additional examples include DNAs that hybridize under stringent conditions with the nucleotide sequence of SEQ ID NO: 1, so long as the adiponectin expression-inducing activity is maintained. KLF9-encoding DNAs may be endogenous DNAs in the cells or exogenously introduced DNAs. Such KLF9-encoding DNAs are preferably equipped with an intrinsic regulatory region of the KLF9 gene in their upstream region.

Cell types in the first and second embodiments are not particularly limited, but are preferably, for example, those derived from mammalian cells, and cell types that usually express adiponectin in vivo are even more preferable. An example of cells that express adiponectin in vivo is adipocytes. When using adipocytes, small adipocytes and swollen hypertrophic adipocytes can be appropriately selected and used. For example, when searching for substances that inhibit biological molecules which suppress the KLF9 expression in the cells of the second embodiment, swollen adipocytes showing decreased expression of adiponectin can be used. Large adipocytes can be prepared by isolating adipocytes from ob/ob mice, or by using adipocytes in which differentiation has not progressed (such as 3T3L1 adipocytes) as a starting material and then referring to the Examples to carry out induction of differentiation. Induction of adipocyte differentiation can be performed by culturing cells in a differentiation-inducing medium.

When the "reporter gene quipped with a KLF9-binding element in the upstream region" in the cells of the first or second embodiment, or the "KLF9-encoding gene" in the cells of the second embodiment is exogenously introduced into cells, such DNA may be carried on a vector or such and then introduced into cells. In such cases, a vector can be appropriately selected and used.

Fourthly, the present invention relates to methods of screening for substances that can induce the expression of adiponectin. The screening method of the first embodiment is a method that uses the cells of the first embodiment. More specifically, the method comprises the steps of:

(1) reacting the cells of the first embodiment with a test substance;

(2) detecting expression of the reporter gene; and (3) selecting a test substance that yields a higher reporter gene expression in cells reacted with the test substance than in cells that have not reacted with the test substance.

The screening method of the second embodiment is a method that uses the cells of the second embodiment, and specifically comprises the steps of:

(1) reacting the cells of the second embodiment with a test substance;

(2) detecting expression of the reporter gene; and (3) selecting a test substance that yields a higher reporter gene expression in cells reacted with the test substance than in cells that have not reacted with the test substance.

Both embodiments have a common aspect in that the substances of interest which can induce expression of the adiponectin gene can be searched, but each has characteristics depending on the functions of the cells to be used. For example, in the first embodiment, cells that carry a reporter gene quipped with a KLF9 binding element are used, thereby enabling the screening of substances that can induce the adiponectin expression by acting on the KLF9-binding element instead of on KLF9. In the second embodiment, cells that additionally carry a KLF9-encoding DNA are used, thereby enabling the screening of substances that inhibit the suppression of KLF9 expression in hypertrophic adipocytes.

Examples of test substances in the first and second embodiments are not particularly limited and include proteins, nucleic acids, and low molecular weight compounds. In addition, they may be natural or synthetic. Nucleic acids can include nucleic acid (DNA and RNA) decoys that mimic the whole or a portion of a KLF9 protein. In addition to naturally occurring nucleotides, nucleic acids may also include those synthesized using artificial nucleotides which do not exist in nature. Low-molecular weight compounds may include compound libraries synthesized by combinatorial chemistry.

An example of reacting cells with a test substance is adding a test substance to a medium in which the cells are being cultured. When the test substance is a nucleic acid, standard gene transfer techniques including the method of coating the test substance with a lipid molecule such as liposome, or salt such as calcium phosphate, and then introducing it into cells via phagocytosis; the method of introducing the test substance into cells using electrical stimulation; microinjection; and gene gun can be used.

The expression of a reporter gene may be detected at the transcriptional level or translational level. Detection of expression at the transcriptional level may be performed by Northern blotting, RT-PCR, real-time PCR, and such. Primers and probes used for these methods can be produced by those skilled in the art by appropriately designing them from nucleotides of reporter genes. In addition to detection methods using specific antibodies, such as Western blotting, immunoprecipitation, ELISA, and RIA, detection of expression at the translational level can be performed by methods that fit properties of the reporter gene products. For fluorescent proteins such as luciferase and GFP, their fluorescence is detected, and for enzymes such as β-galactosidase, reaction with the substrate is detected. In the case of a drug-resistance marker, cells are cultured in a medium containing the drug, and their growth can be used as an index to detect the expression. When quantifying the expression level, any one of the detection methods using specific antibodies, or methods that use fluorescence with measurable intensity as an index are preferably used.

In both the first and second embodiments, the expression levels of the reporter gene in the presence and absence of a test substance are ultimately measured, and test substances that yield a higher reporter gene expression level in their presence than in their absence are selected. Test substances selected herein are important candidates for substances that can promote the adiponectin gene expression.

The screening methods of the present invention may be applied not only to screen for adiponectin expression-inducing substances, but also to search for candidate substances for pharmaceutical agents for preventing and/or treating obesity or obesity-related diseases. Obesity-related diseases, as repeatedly mentioned above, include metabolic diseases such as diabetes and insulin resistance, and heart diseases such as arteriosclerosis. Hypoadiponectinemia is often observed in these diseases. When hypoadiponectinemia is one of the factors determining the onset of these diseases, or a factor that promotes progression of a morbid state, the substances obtained from the above-mentioned screening methods are expected to improve hypoadiponectinemia in patients, and induce prevention, treatment, and alleviation of the pathology of obesity or obesity-related diseases.

Besides the above-mentioned screening method, a convenient screening method includes the method of selecting test substances by using the interaction activity with a KLF9 binding element such as SEQ ID NO: 5 as an index. The interaction activity can be measured using, for example, immunoprecipitation assays or EMSA indicated in the Examples. All prior art references cited in the description are herein incorporated by reference.

EXAMPLES

Herein below, the present invention will be specifically described with reference to the Examples, but it is not to be construed as being limited thereto. The materials and methods used in the Examples are described below.

[Materials and Methods]

1. Materials and General Methods

3-Isobutyl-1-methylxanthine (IBMX), dexamethasone (DEX), NAC, and SP600125 were purchased from Sigma. Other materials were all purchased from supply sources indicated in the cited references (Non-Patent Documents 27, 35, and 36). DNA sequencing was performed on an ABI PRISM 310 Genetic Analyzer (Applied Biosystems) using the PRISM Dye Terminator Cycle Sequencing Kit.

2. Animals and Blood Sample Assay

KLF9 knockout mice have already been reported (Morita, M. et al., Mol. Cell. Biol. 23, 2489-2500 (2003)). 15-Week old ob/ob mice and their wild-type C57BL/6 mice were obtained from Charles River Breeding Laboratories (Wilmington, Mass.). The mice were housed in a colony cage and kept under a twelve hour light/dark cycle. The plasma glucose level was determined using the Glucose B-test (Wako Pure Chemical Industries, Osaka). The Plasma adiponectin level was determined using the Mouse Adiponectin Radioimmunoassay (RIA) Kit (LINCO Research Inc.).

3. cDNA Library

The cDNA library provided by A. Saltiel was used. This library was constructed by inserting cDNAs collected from fully differentiated 3T3-L1 adipocytes into the pGAD-GH GAL4 vector (Ribon, V. et al., Mol. Cell. Biol. 18, 872-879 (1998)). The library contained 10,000,000 transformants which all comprise 1.5 to 3-kb cDNA inserts.

4. Yeast One-Hybrid Cloning

Conventional methods for one-hybrid cloning in yeast, and related experimental manipulations were carried out according to reported procedures (Almoguera, C. et al., J. Biol. Chem. 277, 43866-43872 (2002)). A yeast strain derivative of YM4271 (Clontech) was constructed for one-hybrid cloning. More specifically, a DNA fragment produced by annealing a top strand oligonucleotide, which comprises 32 nucleotides (position −188 to position −157, FIG. 3b, SEQ ID NO: 5) derived from the adiponectin promoter sequence shown below, to its complementary strand was inserted between the XbaI site (end-filled with Klenow DNA polymerase) and EcoRI site of the pHISi plasmid (Clontech).

5'-GAAGCCCAAGCTGGGTTGTACCAGGTTCCCTA-3' (top strand)

YM4271 (Clontech) was transformed with the reaction product to obtain clones carrying a HIS3 reporter gene construct ((G4HSE)×3::HIS3) that comprises an insert in which the annealed fragments form a trimer.

For one-hybrid screening, 1,660,000 primary clones were amplified, and then (32 bp)×3::HIS3 reporter yeast strain was transformed with DNAs prepared from an embryonic cDNA library. Five million yeast transformants were cultured on 15 mM 3-aminotriazole (SD−, His−, Leu+). After 4 to 8 days of growth at 30° C., 22 putative positive yeast clones were selected for further analysis. Two cDNAs encoded the same KLF9.

5. Luciferase Assay

Luciferase assay was performed using cells cultured on a 12-well plate according to previously reported methods (Yamauchi, T. et al., Nature 423, 762-769 (2003), and Shindo, T. et al., Nat. Med. 8, 856-863 (2002)). Luciferase reporter plasmid (0.25 µg) and pSV-β gal (0.1 to 0.4 µg) were simultaneously introduced together with specified amounts of expression plasmid. The total amount of DNA used in each transfection was adjusted to 1.5 µg/well using a control vector DNA. The level of luciferase activity in the transformants was measured using a standard kit (Promega). The measured values were normalized based on the β-galactosidase activity.

6. Electrophoretic Mobility Shift Assay (EMSA)

Electrophoretic mobility shift assay was performed as previously described (Almoguera, C. et al., J. Biol. Chem. 277, 43866-43872 (2002)).

Nucleotide extracts were prepared from 293T cells, 3T3L1 adipocytes, or white adipose tissue according to a reported method (Almoguera, C. et al., J. Biol. Chem. 277, 43866-43872 (2002)). Double-stranded oligonucleotides used for the electrophoretic mobility shift assay were prepared by annealing both strands. Labeled probes (3,000 to 10,000 cpm) and the nuclear extracts were mixed in a reaction solution (20 µL: 10 mM Tris-HCl (pH7.6), 50 mM KCl, 0.05 mM EDTA, 2.5 mM $MgCl_2$, 8.5% glycerol, 1 mM dithiothreitol, 0.5 µg/mL of poly(dI-dC), 0.1% Triton X, and 1 mg/mL of skim milk), and incubated for 30 minutes on ice. The DNA-protein complexes were fractionated on a 4.6% polyacrylamide gel at 140 V for 1 hour at 4° C. The Gel was dried and exposed using a BAS2000 filter with BAStation software (Fuji Photo Film).

When competition experiments were performed, at least a 100-fold molar excess of unlabeled DNAs relative to labeled DNAs were added to the above-mentioned reaction solution before adding the labeled probe. In the supershift experiments, gel shift reactions were carried out by first incubating with a polyclonal antibody (2 to 10 µg) against KLF9, KLF3, or NF-κBp65 on ice.

7. Retrovirus Production and Infection $10^7$ Plat-E packaging cells (Morita, S. et al., Gene Ther. 7, 1063-1066 (2000)) were transiently introduced with 10 µg of mouse KLF9 using Lipofectamine PLUS (Life Technology), and after incubation for 24 hours, the supernatant (10 mL) was collected. The supernatant was diluted 20 times by adding 10 µg/mL of Polybrene (hexadimethrine bromide, Sigma) and then used to infect 3T3L1 adipocytes at an estimated multiplicity of infection of 0.3.

8. Plasmids

Luciferase gene constructs comprising the 1367-bp (−1367 to +35; SEQ ID NO: 4), 527-bp (−527 to +35), 217-bp (−217 to +35), or 127-bp (−127 to +35) fragment of the adiponectin promoter ("pAdiponectin 1367-Luc", "pAdiponectin527-Luc", "pAdiponectin217-Luc", and "pAdiponectin127-Luc", respectively) were subcloned into a pGL2-Basic Vector or PGL2-Promoter Vector (Promega).

9. Expression in Mammalian Cells

KLF3 or KLF9 expression vectors were constructed by ligating to the EcoRI/Not site of pcCNA3.1. DNA transfection into 293T or 3T3L1 adipocytes was carried out by a lipofection method using "Lipofectamine PLUS" (Gibco BRL).

10. Studies Using 3T3L1 Cells

3T3L1 cells were cultured in DMEM with 10% fetal calf serum, and induction of differentiation into fat-producing cells was carried out according to previously reported methods (Yamauchi, T et al., Nat. Genet. 30, 221-226 (2002)). As a simple explanation, 3T3L1 cells were first cultured and grown to confluence. Two days later, the medium was replaced with a standard differentiation-inducing medium (containing 0.5 mM IBMX, 1 µM DEX, 5 µg/mL of insulin, 10% FBS, 50 units/mL of penicillin, and 50 µg/mL of streptomycin), and medium exchange was performed daily or every two days. Glucose uptake was determined by known methods (Yamauchi, T. et al., Nat. Med. 8, 1288-1295 (2002)). The cell lysate was extracted, and its TG content was determined by known methods (Yamauchi, T. et al., Nat. Med. 7, 941-946 (2001)).

11. RNA Interference

Each of the complementary single stranded RNAs were chemically synthesized and annealed to each other to prepare siRNAs. 3T3L1 adipocytes which reached approximately 60% to 70% confluence were introduced with the siRNAs using Lipofectamine PLUS (Life Technology) (Yamauchi, T. et al., Nature 423, 762-769 (2003)). It was confirmed before use in advance that these KLF9 and KLF3 siRNA sequences were able to suppress KLF9 and KLF3 expression, respectively, when introduced. The cells were lysed 72 and 96 hours after siRNA transfection, and the expression products and such were analyzed.

12. Northern Blot Analysis and Quantitative Analysis of Transcripts by Real-Time PCR Total RNAs from cells or tissues were prepared using TRIzol (Gibco/BRL) according to the manufacturer's instructions. For Northern blot analysis, equal amounts of total RNAs from each group were pooled (total of 10 µg), and subjected to formalin-denatured agarose gel electrophoresis. After electrophoresis, the RNAs were transferred to a nylon membrane (Hybond N; Amersham Pharmacia Biotech). The filter was hybridized with each of the cDNA probes produced by labeling mouse KLF9 and mouse KLF3 cDNAs with [$^{32}$P] dCTP. The obtained bands were visualized by exposure to BAS2000 filters with BAStation software (Fuji Photo Film).

The mRNAs were quantified by real-time PCR (Yamauchi, T. et al., Nature 423, 762-769 (2003)). Primer sets and probes were designed using the "Primer Express 1.5a" software, and were purchased from ABI (ABI Prism; Perkin-Elmer Applied Biosystems, Foster City, Calif.). Relative amounts were normalized to the amount of actin transcript in the same cDNAs (Yamauchi, T. et al., Nature 423, 762-769 (2003)).

13. Preparation and Immunoblot Analysis of Nuclear Extracts

Nuclear extracts were prepared according to known methods (Almoguera, C. et al., J. Biol. Chem. 277, 43866-43872 (2002)). Samples of nuclear proteins (30 μg) were analyzed by immunoblots using rabbit immunoglobulin G (IgG) against KLF9 (Zhang, D. et al., Endocrinology 143, 62-73 (2002)) or KLF3 (Crossley, M. et al., Mol. Cell Biol. 16, 1695-1705 (1996)), and then horseradish peroxidase-bound mouse or rabbit IgG with an ECL kit (Amersham Pharmacia Biotech).

14. Chromatin Immunoprecipitation Assay

Dormant 3T3L1 adipocytes were fixed in 1% formaldehyde. The fixed chromosome sample was analyzed by a method in which a few changes were made to the known immunoprecipitation method (Shindo, T. et al., Nat. Med. 8, 856-863 (2002)). Protein A (Upstate) was used to recover the precipitates.

15. Measurement of Antioxidant Activity

Cayman chemical antioxidant assay was used to measure the total antioxidative ability of plasma, serum, urine, stool, or cell lysate. Since water-soluble and lipid-soluble antioxidants cannot be separated using this protocol, the combined antioxidative activity of all ingredients including vitamins, proteins, lipids, glutathione, and uric acid was analyzed. The analysis was based on measuring the activity of the antioxidant in a sample to inhibit the oxidation of $ABTS^R$ (2,2'-Azino-di-[3-ethylbenzthiazoline sulfonate]) to $ABTS^{R+}$ by metmyoglobin. The amount of sample that induces absorbance inhibition at 750 nm depends on its concentration. The sample's antioxidative activity of inhibiting the ABTS oxidation was compared with the antioxidative activity of Trolox, a water-soluble tocopherol analog, and was quantified by normalization to millimolar concentrations of Trolox.

Example 1

Adiponectin mRNA Level is Decreased in Hypertrophic 3T3L1 Adipocytes

Adiponectin mRNA level is decreased in obesity and this has been reported to act as a cause for the development of obesity-related insulin resistance. An objective of the present invention is to isolate transcription factors that cause the decrease of adiponectin expression in obesity. To pursue this objective, an in vitro hypertrophic adipocyte model was used, and the effect of adipocyte hypertrophy on adiponectin gene expression was analyzed.

Figure 1:
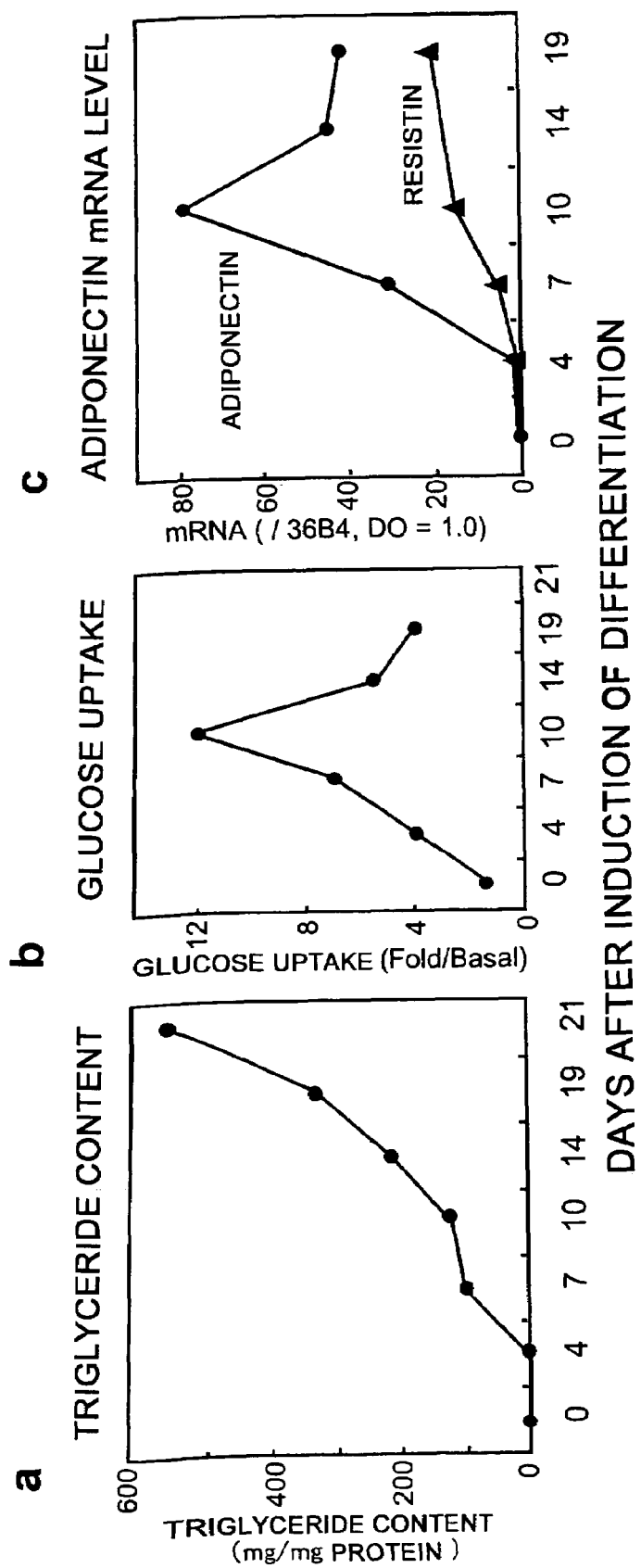
FIG. 1 shows graphs indicating the (a) triglyceride (TG) content, (b) glucose uptake, and (c) mRNA levels of adiponectin and resistin in 3T3L1 cells during adipocyte differentiation and hypertrophy. The mRNA levels of adiponectin and resistin (c) in 3T3L1 adipocytes during adipocyte differentiation and hypertrophy were measured by TaqMan real-time reverse transcription-PCR assay. The resulting expression levels of adiponectin or resistin are indicated as relative values normalized using the 36B4 mRNA level as a standard. Each data is an average obtained from a series of three independent experiments. Adipocyte hypertrophy reduces the adiponectin mRNA level in 3T3L1 adipocytes, which is accompanied by a decrease in glucose uptake.

Interestingly, 19 days after induction of adipocyte differentiation (day 19), the triglyceride content of 3T3L1 adipocytes increased (FIG. 1a); insulin resistance such as decreased glucose uptake in response to insulin was observed (FIG. 1b); an even higher insulin resistance that induces adipokines such as resistin was exhibited (FIG. 1c); and adiponectin mRNA expression was found to decrease in comparison to 3T3L1 adipocytes ten days after induction of adipocyte differentiation (day 10) (FIG. 1c). Similar to changes observed at the mRNA level, the adiponectin protein expression level was also decreased in hypertrophic adipocytes (data not shown). The above suggested that the decrease in the adiponectin gene expression in hypertrophic adipocytes was caused by a decrease at the transcriptional level.

Example 2

A Non-TNFα Signal Transduction Pathway is Involved in the Decrease of Adiponectin Expression in Hypertrophic Adipocytes The promoter analysis of the 5'-flanking region of the adiponectin gene has previously identified the C/EBP transcription factor that induces adipocyte-specific expression (Schaffler, A. et al., Biochim. Biophys. Acta. 1399, 187-197 (1998), and Saito, K. et al., Biol. Pharm. Bull. 22, 1158-1162 (1999)). However, the upstream factor that determines the decrease of adiponectin expression in hypertrophic adipocytes observed in obesity has not been identified. Interestingly, the promoter activity of the region comprising −1367 to +35 of the adiponectin promoter region linked to a luciferase gene was higher in the small adipocytes (day 10) than in precursor adipocytes (day 0) or large adipocytes (day 19) (FIG. 2a), and this correlated with the adiponectin expression level.

TNFα, which has been shown to decrease adiponectin expression, increases in hypertrophic adipocytes. Therefore, it seemed reasonable to predict that TNFα is the causative factor that decreases the adiponectin expression in hypertrophic adipocytes (Barth, N. et al., Diabetologia 45, 1425-1433 (2002)).

Figure 2:
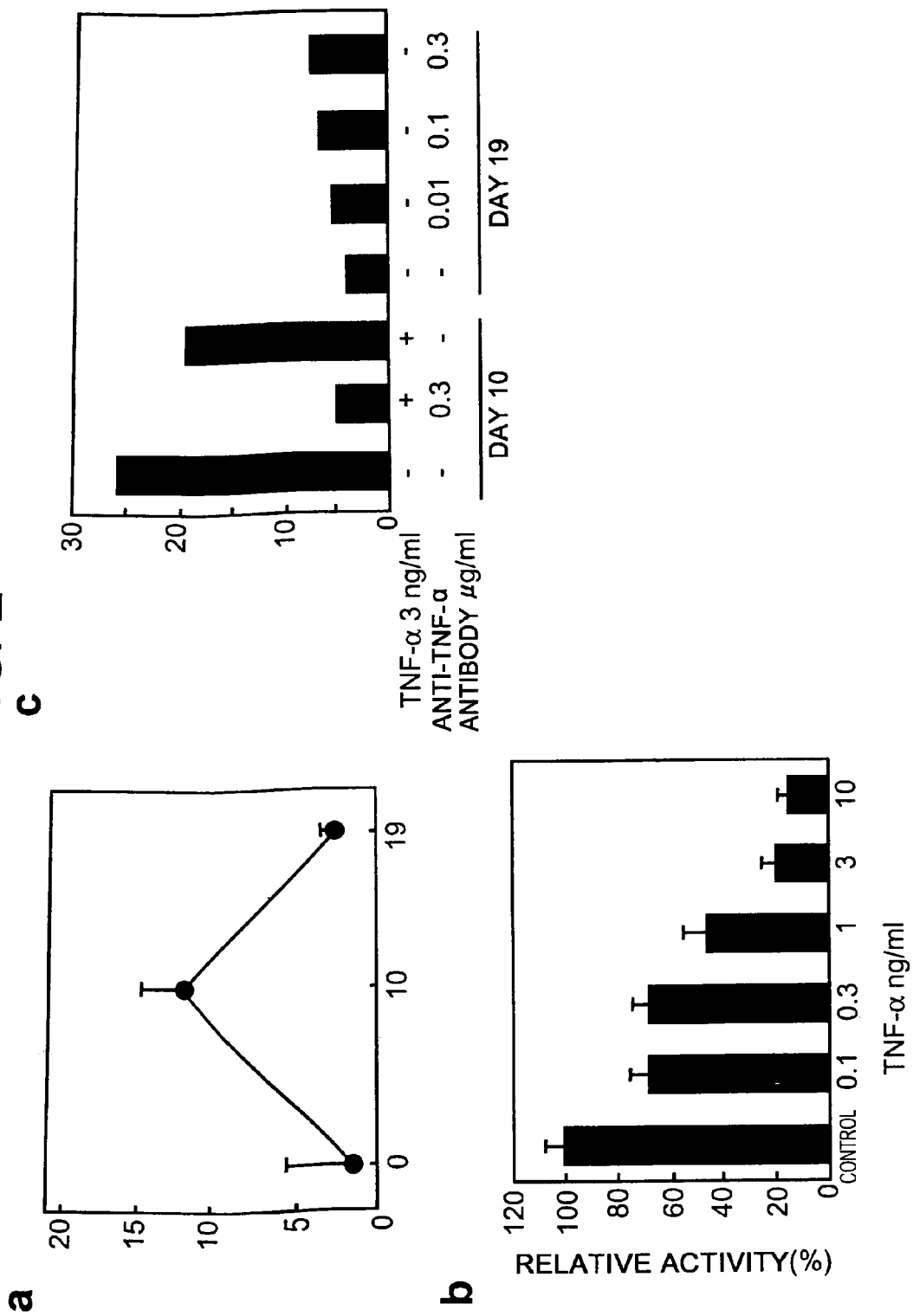
FIG. 2 shows results of measuring the adiponectin promoter activity in 3T3L1 cells during adipocyte differentiation and hypertrophy. Each of the graphs shows results of determining: (a) adiponectin promoter activity in 3T3L1 cells during adipocyte differentiation and hypertrophy; (b) adiponectin promoter activity in 3T3L1 cells incubated with the indicated concentrations of TNFα 10 days after the induction of differentiation; and (c) adiponectin promoter activity in TNFα (3 ng/mL)-treated or untreated 3T3L1 cells incubated with an anti-TNFα antibody 10 or 19 days after induction of differentiation. The (−1367/+35) of the adiponectin promoter-luciferase gene (Luc) expression vector was transiently transfected into 3T3L1 cells. The results in (b) are shown as relative values taking the activity without TNF-α addition as 100%. Each of the bars in (b) shows the mean±SE (n=5 to 7) relative to untreated cells). The adiponectin promoter activity in hypertrophic adipocytes is decreased because of the existence of non-TNFα signal transduction pathways.

Incubation of small adipocytes (day 10) with TNFα actually decreased the adiponectin gene promoter activity (FIG. 2b). However, neutralization of TNFα using antibodies did not have any effect on the decreased adiponectin gene promoter activity in hypertrophic adipocytes (day 19) (FIG. 2c). These data suggested the existence of a non-TNFα signal transduction pathway that causes the decrease of adiponectin expression in hypertrophic adipocytes.

Example 3

Figure 3:
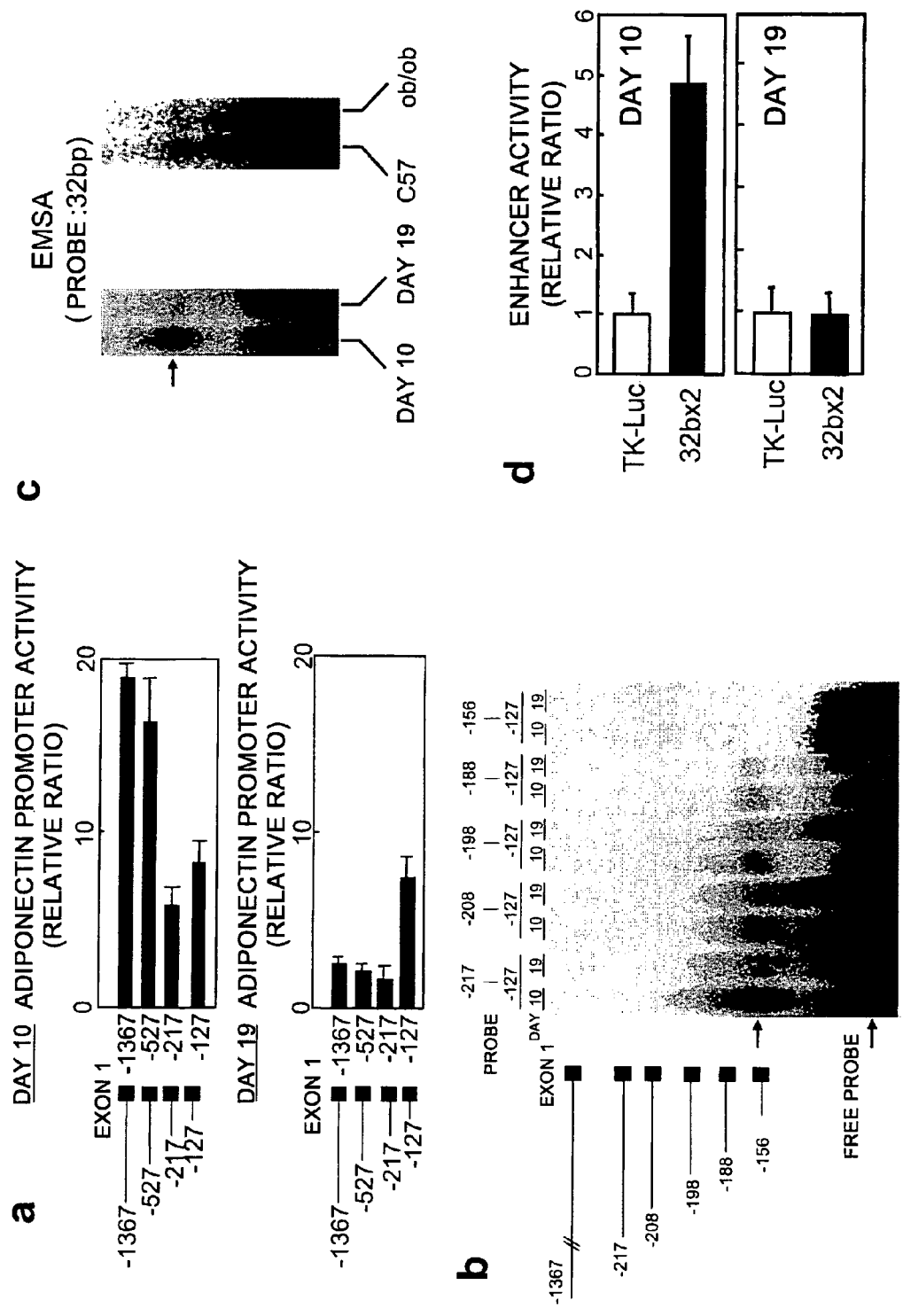
FIG. 3 shows results of analyzing the adiponectin promoter region. (a) Graphs indicating results of examining the reporter (luciferase) activity when a reporter gene equipped with a 5'-deleted adiponectin promoter was incorporated into a vector and this vector was transiently introduced into 3T3L1 adipocytes 10 or 19 days after induction (day 10 or day 19, respectively). (b) A photograph showing the results of subjecting nuclear protein extracts prepared from 3T3L1 adipocytes (day 10 or day 19) to EMSA analysis, by using the 5'-deleted adiponectin promoter sequences shown in the figure as $^{32}$P-labeled probes. The data shown are representative results of a series of three independent experiments. (c) Photographs showing the results of preparing nuclear protein extracts from 3T3L1 adipocytes (day 10 or day 19), or white adipose tissue (WAT) from lean control mice C57 or from obese mouse model ob/ob mice, and subjecting them to EMSA analysis using the adiponectin promoter (−188/−157) sequence as a $^{32}$P-labeled probe. (d) Graphs showing results of assaying the luciferase activity when the −188/−157 fragment was inserted upstream of an enhancer-free pGL2-tK-Luc vector, and this vector was introduced into 3T3L1 adipocytes (day 10 and day 19). The results in (d) are shown as ratios relative to the control vector values. The bars show the mean±SE of three independent experiments. The data of panels b and c show representative results obtained from a series of three independent experiments. In hypertrophic adipocytes, the adiponectin promoter is regulated through a proximal 32-bp promoter element.

The Adiponectin Promoter is Regulated Through a Proximal 32-bp Promoter Element in Hypertrophic Adipocytes Functional 5' deletion analysis was performed to identify the promoter region involved in the nonresponsiveness of the adiponectin gene in hypertrophic adipocytes. Studies carried out so far have revealed that deletion of the −1367 to −217 region does not substantially affect the adiponectin promoter activity in day-19 3T3L1 adipocytes (FIG. 3a). In contrast, when another 90 nucleotides were deleted in day-19 3T3L1 adipocytes, the adiponectin promoter activity recovered. This suggested that an essential regulatory element is included in −217/−127.

Further functional 5' deletion analysis was performed using EMSA to identify the element to which the transcription factor binds. Analysis of the −217/−127 promoter region using EMSA showed that a major complex binds to this element in greater numbers in day-10 3T3L1 adipocytes than in day-19 3T3L1 adipocytes (FIG. 3b). Deletion of the −217 to −189 region did not substantially affect the amount of binding protein in the nuclear extract derived from day-10 3T3L1 adipocytes (FIG. 3b). In contrast, when another 32 nucleotides were deleted, the amount of binding protein in day-10 3T3L1 adipocytes remarkably decreased (FIG. 3b), and this suggested that −188/−157 includes an essential binding element. Importantly, the amount of a major complex that bound to the 32-bp element (−188/−157) was less in the obese model ob/ob mice and in day-19 3T3L1 adipocytes than in the lean control C57B6 mice and day-10 3T3L1 adipocytes (FIG. 3c).

This element was incorporated into a promoter system and a functional analysis was carried out to examine the enhancer properties of this promoter region in detail (FIG. 3d). The presence of this −188/−157 element increased the basal transcriptional activity five times in day-10 3T3L1 adipocytes when compared with only the control pGL-2-tk-Luc vector, but in day-19 cells, a similar increase was not observed (FIG. 3d).

Example 4

Yeast One-Hybrid Cloning of the 32-bp Element-Binding Protein

The yeast one-hybrid cloning approach was used to isolate a trans-factor that downregulates the adiponectin gene promoter in hypertrophic adipocytes (Almoguera, C. et al., J. Biol. Chem. 277, 43866-43872 (2002)). The 32-bp element was used as a bait. This sequence was trimerized, incorporated into the upstream of the HIS3 reporter gene, and then introduced into yeast cells to produce (32 bp)×3::HIS3 reporter yeast strain.

Twenty-two positive colonies were obtained. Different groups are included in these clones. They were separated into two groups according to their nucleotide and putative amino acid sequences. In one group, ten independent cDNA isolates and two independent cDNA isolates encode transcription factors that belong to the Kruppel-like transcription factor (KLF) family (Shindo, T. et al., Nat. Med. 8, 856-863 (2002), and Morita, M. et al., Mol. Cell. Biol. 23, 2489-2500 (2003)), Kruppel-like factors 3 and 9, respectively. The other group consisted of four independent cDNA isolates encoding a transcription factor, NF-κBp65 (Suzawa, M. et al., Nat. Cell Biol. 5, 224-230 (2003)).

Example 5

EMSA Showed that the 32-bp Binding Complex Comprises KLF9 In Vitro and In Vivo

Figure 4:
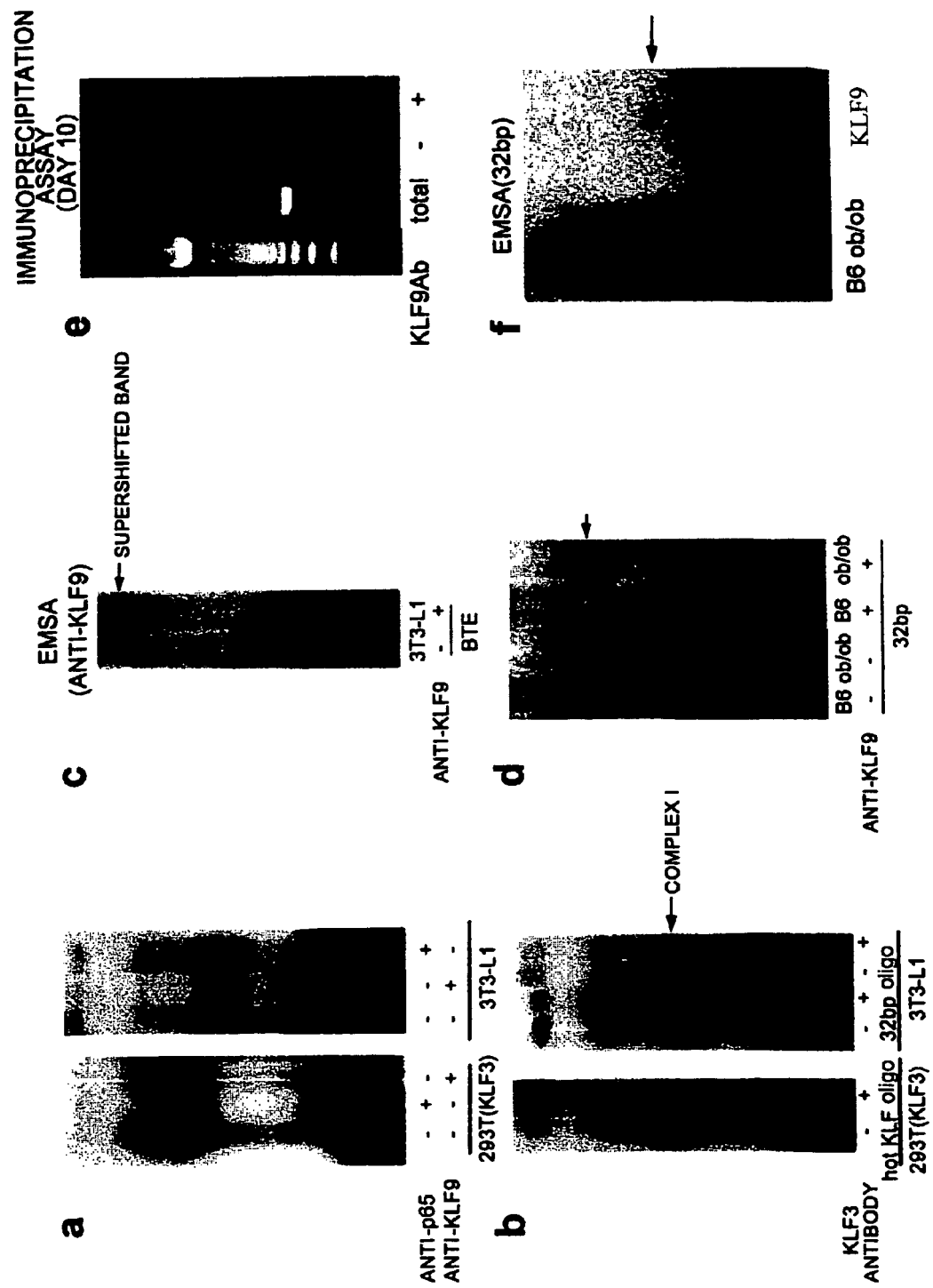
FIG. 4 presents photographs showing the results of analyzing factors that bind to the adiponectin promoter region in the nuclear extract of 3T3L1 adipocytes (day 10). Panels a to d, and f show results of the EMSA analysis. The photographs show (a) results of an EMSA analysis when the nuclear extracts from 3T3L1 adipocytes (day 10) or 293T cells, and radiolabeled NF-κB consensus sequence (p65 site) were incubated in the presence or absence of an antibody that specifically recognizes KLF9 or NF-κBp65; (b) (right panel) results of incubating the nuclear extract of 3T3L1 adipocytes (two lanes on the left: day 10, two lanes on the right: day 19) with a labeled 32-bp oligonucleotide probe of the adiponectin promoter region (−188/−157) in the presence or absence of an anti-KLF3 antibody, (left panel) results of an EMSA analysis when the nuclear extract from 293T cells and KLF oligo (KLF consensus sequence) were incubated in the presence or absence of an anti-KLF3 antibody; (c) results of reacting the nuclear extract from 3T3L1 adipocytes (day 10) with the KLF9 consensus sequence (BTE) in the presence or absence of an anti-KLF9 antibody; (d) results of reacting WAT from lean control mice C57BL6 (B6) or from obese mouse model ob/ob mice, with the 32-bp fragment and an anti-KLF9 antibody; and (f) results of incubating with the 32-bp fragment, purified FLAG-tag KLF9, or WAT from B6 or from obese mouse model ob/ob mice. The arrows in the figures indicate a supershifted specific complex. (e) A photograph showing results of the chromatin immunoprecipitation assay with KLF9 bound to an endogenous adiponectin promoter in 3T3L1 adipocytes (day 10). The data shows representative results obtained from a series of three independent experiments. EMSA analyses showed that the 32-bp binding complex contains KLF9 in vitro and in vivo.

EMSA supershift experiments were performed using specific antibodies that recognize KLF3, KLF9, or NF-κBp65 to further identify nuclear factors that bind to the 32 bp element. These studies found that complex I in the 3T3L1 adipocytes (day 10) comprises the KLF9 protein (FIG. 4a right, lanes 1 and 2). In contrast, in small adipocytes, neither KLF3 (FIG. 4b) nor NF-κBp65 (FIG. 4a right, lanes 1 and 3) was detected in vitro. In the control EMSA, specificity of the KLF9 antibody was confirmed by using nuclear extracts of 293T cells with a labeled KLF9 consensus region as a probe (FIG. 4c). The function of a KLF3 antibody (FIG. 4b left) or NF-κBp65 antibody (FIG. 4a left) was confirmed by performing a supershift assay that uses 293T cells expressing a nuclear extract which is a cognate protein, and a KLF3 consensus site or NF-κB consensus site (p65 site) as a radiolabeled probe. Importantly, the KLF9 antibody decreased the amount of the 32-bp binding protein (FIG. 4d), and this suggested that the 32-bp binding protein (complex) comprises KLF9 even in vivo.

EMSA competition analysis was carried out to confirm these results. Complete competitive inhibition of complex I was found to take place with an excess amount of BTE, a KLF consensus sequence (data not shown). In contrast, the NF-κB consensus sequence was clearly not effective (data not shown).

Chromatin immunoprecipitation assay was performed to further confirm these findings. KLF9 was found to actually bind to the endogenous adiponectin promoter region comprising the 32-bp site (FIG. 4e). Furthermore, purified KLF9 also showed nearly the same inhibition of the 32-bp fragment as that by a nuclear extract prepared from adipocytes or adipose tissue (FIG. 4f).

Example 6

Figure 5:
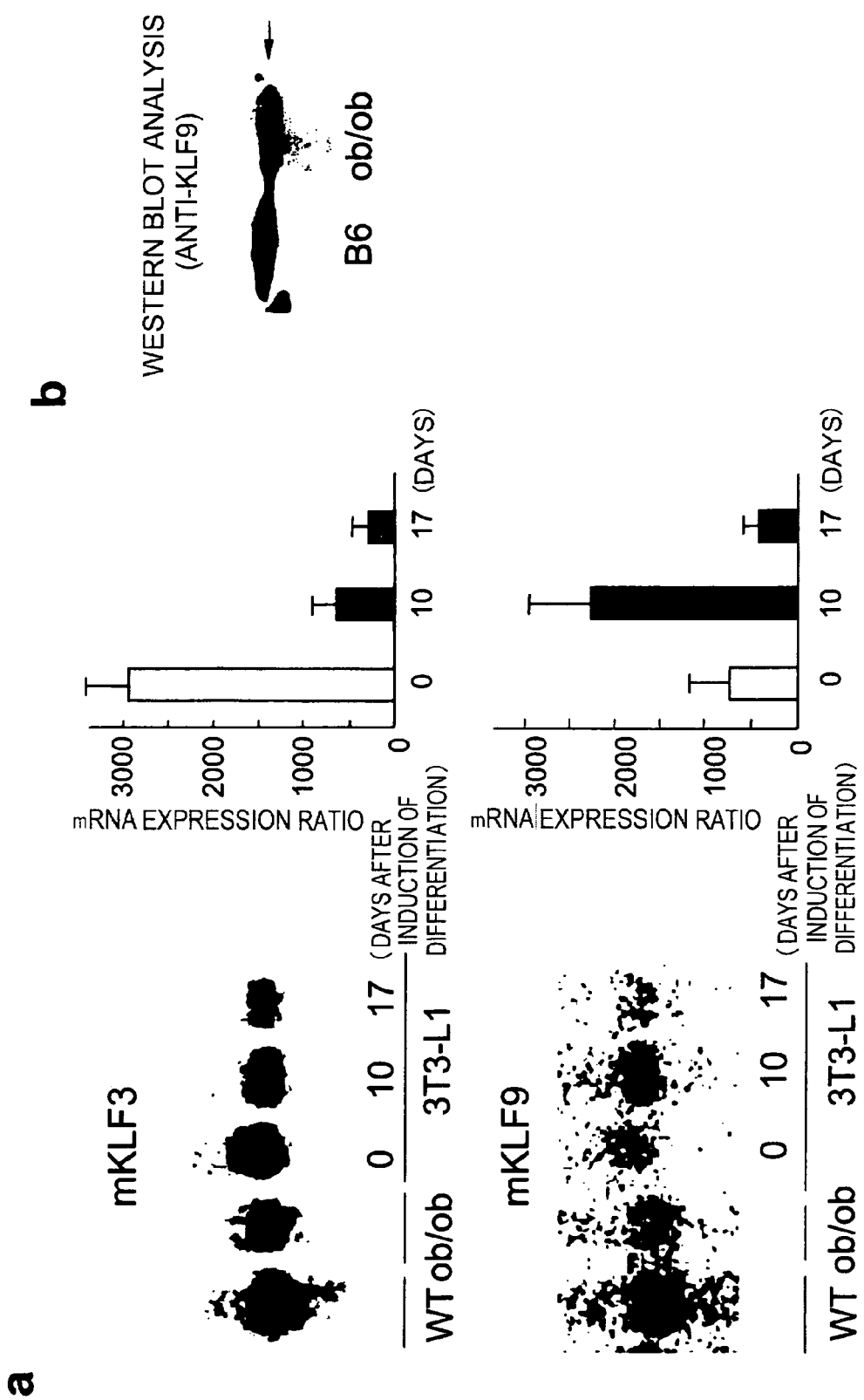
FIG. 5 presents photographs and diagrams showing results of analyzing the expression levels of KLF3 and KLF9 in adipocytes. (a and b) Photographs of Northern blots that analyze the expression levels of KLF3 mRNA (a, top) or KLF9 mRNA (a, lower) in 3T3L1 adipocytes, in which an indicated number of days had passed since differentiation is induced, and in WAT obtained from lean control mice C57BL6 or from obese mouse model ob/ob mice (a to b); graphs that quantify the band intensity; and a photograph showing results of analyzing the expression level of mKLF9 protein (b) by Western blotting. The arrow in (b) indicates KLF9. Each of the bars in the graphs shown in (a) represents the mean SE (n=3 to 5). KLF9 expression increased during adipocyte differentiation, but decreased during adipocyte hypertrophy.

KLF9 Expression Increased as Adipocytes Differentiated, But Decreased with the Hypertrophy of Adipocytes Next, expression of KLF3 and KLF9 during adipocyte differentiation and adipocyte hypertrophy was investigated. KLF9 expression increased during adipocyte differentiation, but decreased during adipocyte hypertrophy (FIG. 5a, bottom). In contrast, the KLF3 expression level decreased during both the differentiation and hypertrophy of adipocytes (FIG. 5a, top). Furthermore, the mRNA level (FIG. 5a) and protein level (FIG. 5b) of KLF9 were higher in the lean control mice, C57BL6, than in the obese ob/ob mice. This result was predicted to correlate with the amount of the 32-bp binding protein, and strongly suggested the possibility that the KLF9 expression level can regulate the activity of the adiponectin promoter as well as the adiponectin expression level.

Example 7

Figure 6:
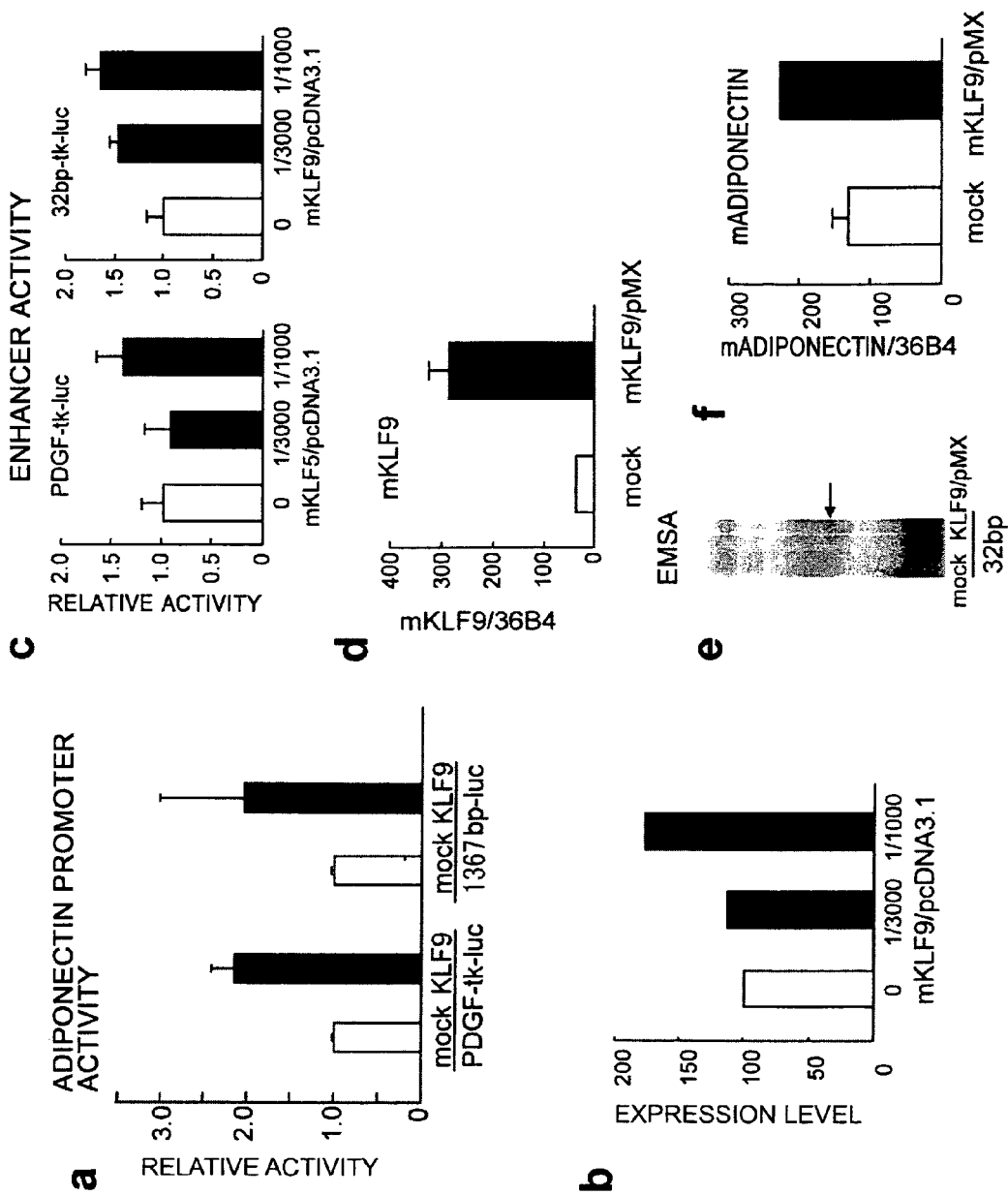
FIG. 6 presents diagrams and a photograph showing results of analyzing the effect of KLF9 overexpression on adiponectin expression. (a) Results of introducing into 3T3L1 adipocytes (day 19) a vector expressing KLF9 (KLF9/pcDNA3.1) and a vector ("136Thp-Luc") equipped with a reporter (luciferase) gene downstream of the adiponectin promoter ("−1367/+35"), and analyzing the effect of KLF9 overexpression. The results are shown as relative activities taking "Mock" (only pcDNA3.1) as 1. PDGF is a positive control that is equipped with a KLF recognition sequence and induces the KLF family expression. (b) Results of measuring the expression level of KLF9 mRNA in 3T3L1 adipocytes (day 19) by Taq-man PCR, when the cells were introduced with KLF9/pcDNA3.1 by lipofection. 1/3000 and 1/1000 indicate the dilution ratios when vector introduction was performed by lipofection, and "0" indicates no introduction. (c)

KLF9 Expression Increased the Activities of the Enhancer and Adiponectin Promoter, the 32-bp Binding Protein Level, and the Adiponectin Expression KLF9 was transiently overexpressed in 3T3L1 adipocytes (day 19) (FIGS. 6a-c) or 3T3L1 adipocytes (day 19), using retroviruses (FIGS. 6d-f) to analyze the enhancer activity, adiponectin promoter activity, 32-bp binding protein level, and adiponectin expression level (FIG. 6). Overexpression of KLF9 in 3T3L1 adipocytes (day 19) increased the adiponectin promoter activity (−1367/+35) (FIG. 6a), 32-bp (−188/−157) enhancer activity (FIG. 6c right panel), and 32-bp binding protein level (FIG. 6e). It was demonstrated that KLF9 can increase adiponectin promoter activity (FIG. 6a) and that the 32-bp element is highly responsive towards KLF9 (FIGS. 6c, e).

Furthermore, constant overexpression of KLF9 in 3T3L1 adipocytes by a retrovirus (FIG. 6d) increased adiponectin expression (FIG. 6f). These data suggested that overexpression of KLF9 in 3T3L1 adipocytes (day 19) can restore the 32-bp binding protein level, 32-bp enhancer activity, adiponectin promoter activity, and adiponectin expression to those observed in 3T3L1 adipocytes (day 10).

Example 8

Suppression of KLF9 Expression by siRNAs Decreased the 32-bp Binding Protein Level and Adiponectin Expression In Vitro Next, to study the functional importance of KLF9 on adiponectin expression, the effect of decreased KLF9 expression was examined. siRNA (Miyagishi, M. & Taira, K. Nat. Biotechnol. 20, 497-500 (2002)) was used as a method for suppressing KLF9 expression. Suppression of KLF9 expression by siRNAs (FIG. 7a) did not have a large effect on KLF3 expression (FIG. 7a). On the other hand, suppression of KLF9 expression significantly decreased the expression level of the 32-bp binding protein (FIG. 7b), and at the same time, drastically decreased the adiponectin expression in 3T3L1 adipocytes (day 10) (FIG. 7a). These data show that KLF9 is necessary for the formation of the 32-bp enhancer-binding protein complex and the adiponectin expression.

Example 9

Disruption of KLF9 Expression by Gene Targeting Decreased the 32-bp Binding Protein Level and the Plasma Adiponectin Level In Vivo Next, to study the functional relationship between adiponectin expression and KLF9 in vivo, the phenotypes of KLF9 knockout mice were analyzed (FIG. 8) (Morita, M. et al., Mol. Cell. Biol. 23, 2489-2500 (2003)). Interestingly, the 32-bp binding protein was not detected in the nuclear extract derived from KLF9 knockout mice "WAT" (FIG. 8). Importantly, despite that the weight of KLF9 knockout mice was lower than that of the control wildtype littermates, the plasma adiponectin level in KLF9 knockout mice was lower than that of the control wildtype littermates (FIG. 8). In contrast, no difference in the plasma adiponectin level was observed between KLF3 knockout mice and their control wildtype littermates (data not shown). These data suggested that KLF9 plays an important role in the regulation of the adiponectin level in vivo.

Example 10

Adipocyte hypertrophy is a Regulation Mechanism of KLF9 Expression in Adipocytes Next, whether adipocyte hypertrophy is a regulation mechanism of KLF9 expression in adipocytes was analyzed. KLF9 expression has been reported to be induced by thyroid hormones which are known to be involved in energy consumption (Morita, M. et al., Mol. Cell. Biol. 23, 2489-2500 (2003)). Therefore, expression of the thyroid hormone receptor a was first examined in vitro and in vivo. Interestingly, expression level of the thyroid hormone receptor a was lower in 3T3L1 large adipocytes (day 19) than in 3T3L1 small adipocytes (day 10), and lower in obese mouse model ob/ob mice than in lean control mice C57BL6 (FIGS. 9a, b). Furthermore, incubation of thyroid hormone with 3T3L1 adipocytes (day 19) led to an increase in KLF9 expression (FIG. 9c).

The KLF9 promoter is reported to comprise an AP-1 site (Chen, A. et al., Mol. Cell. Biol. 20, 2818-2826 (2000)); thus, it is hypothesized that oxidative stress may be involved in the KLF9 expression regulation by adipocyte hypertrophy. Interestingly, an inhibitor of c-jun N-terminal kinase (JNK)/stress-activated protein kinase (SAPK) together with antioxidative N-acetyl cysteine (NAC) increased the expression of adiponectin (FIG. 9e) as well as that of KLF9 (FIG. 9d). Such increase in expression did not involve thyroid hormone receptor α (data not shown). These data suggest a possibility that the upstream mechanism for increasing KLF9 expression partly comprises at least two pathways (one is the thyroid hormone receptor (TR) α signal transduction pathway, and the other is unrelated to TRα expression, but depends on oxidative stress).

To further confirm the above-mentioned hypothesis, the change in oxidative stress during adipocyte hypertrophy was measured. Genomic DNAs extracted from 3T3L1 cells (day 10 and day 19) were degraded, and the amount of 8-OHdG (oxidized form of dG) in the degradation products of genomic DNA was measured by ELISA using a specific antibody. The amount of 8-OHdG increased along with differentiation (FIG. 10). The change of antioxidative activity that accompanies adipocyte hypertrophy was examined to analyze the cause of the hypertrophy-accompanying increase in 8-OHdG. Antioxidative activity was detected as the activity of metmyoglobin to prevent formation of ABTS radicals in 3T3L1 cell lysates (day 10 and day 19). Antioxidative activity was shown to decrease following adipocyte hypertrophy (FIG. 11).

INDUSTRIAL APPLICABILITY

Molecular characterization of KLF9 is expected to promote understanding of the molecular mechanism of adiponectin/Acrp30 downregulation in obesity and obesity-related diseases such as diabetes and atherosclerosis, as well as design of novel antidiabetic and antiatherosclerotic agents whose molecular target is KLF9.

The invention claimed is:

1. A composition comprising:
   (1) a DNA molecule comprising the nucleotide sequence of SEQ ID NO:1; or
   (2) a DNA molecule that hybridizes with the nucleotide sequence of SEQ ID NO:1 under stringent conditions of 6×SSC and 40% formamide at 25° C. for hybridization, and 1×SSC at 55° C. for washing.

2. An isolated cell comprising (i) a DNA molecule comprising a reporter gene operably linked to an enhancer element comprising the nucleotide sequence of SEQ ID NO: 5 and (ii) the DNA molecule of (1) or (2):
   (1) a DNA molecule comprising the nucleotide sequence of SEQ ID NO:1; or
   (2) a DNA molecule that hybridizes with the nucleotide sequence of SEQ ID NO:1 under stringent conditions of 6×SSC and 40% formamide at 25° C. for hybridization, and 1×SSC at 55° C. washing.

3. The cell of claim 2, wherein said cell is an adipocyte.

4. The cell of claim 2, wherein said cell is a hypertrophic adipocyte.

5. A method of screening for a substance that can induce adiponectin expression comprising
   (a) reacting the cell of claim 2 with a test substance;
   (b) detecting expression of a reporter gene; and
   (c) selecting a test substance that yields a higher reporter gene expression in the cell treated with the test substance than in the cell that has not reacted with the test substance.

6. The composition of claim 1, wherein the DNA of (2) is a DNA encoding a polypeptide comprising the amino acid sequence of SEQ ID NO: 2.

7. The composition of claim 1, further comprising a vector comprising the DNA molecule of (1) or (2).

8. The cell of claim 2, wherein said cell comprises a vector carrying the DNA of (i) and a vector carrying the DNA of (ii).

9. The cell of claim 2, wherein the DNA of (2) is a DNA encoding a polypeptide comprising the amino acid sequence of SEQ ID NO: 2.

* * * * *